United States Patent
Morokawa et al.

(10) Patent No.: US 7,084,976 B2
(45) Date of Patent: Aug. 1, 2006

(54) CONCENTRATION MEASURING INSTRUMENT

(75) Inventors: Shigeru Morokawa, Higashiyamato (JP); Takakazu Yano, Tokyo (JP); Kenji Matsumoto, Tokyo (JP); Hiroyuki Uematsu, Tanashi (JP)

(73) Assignee: Citizen Watch Co., Ltd., Tokyo (JP)

( * ) Notice: Subject to any disclaimer, the term of this patent is extended or adjusted under 35 U.S.C. 154(b) by 343 days.

(21) Appl. No.: 10/416,200

(22) PCT Filed: Sep. 28, 2001

(86) PCT No.: PCT/JP01/08589

§ 371 (c)(1),
(2), (4) Date: May 8, 2003

(87) PCT Pub. No.: WO02/38048

PCT Pub. Date: May 16, 2002

(65) Prior Publication Data

US 2004/0012783 A1    Jan. 22, 2004

(30) Foreign Application Priority Data

Nov. 10, 2000 (JP) .............................. 2000-342989

(51) Int. Cl.
*G01J 4/00* (2006.01)

(52) U.S. Cl. ........................ 356/364; 356/39; 356/368; 356/367; 250/225

(58) Field of Classification Search ................. 356/39, 356/364–370; 250/225; 600/316, 322
See application file for complete search history.

(56) References Cited

U.S. PATENT DOCUMENTS

| | | | | |
|---|---|---|---|---|
| 5,209,231 A | * | 5/1993 | Cote et al. | 600/310 |
| 5,788,632 A | * | 8/1998 | Pezzaniti et al. | 600/316 |
| 6,167,019 A | * | 12/2000 | Tsuchiya et al. | 369/112.02 |
| 6,370,407 B1 | * | 4/2002 | Kroeger et al. | 600/319 |
| 6,620,622 B1 | * | 9/2003 | Kawamura | 436/164 |
| 2003/0137650 A1 | * | 7/2003 | Fine et al. | 356/39 |

FOREIGN PATENT DOCUMENTS

| | | |
|---|---|---|
| EP | 0 663 604 A1 | 7/1995 |
| JP | 58-17342 | 2/1983 |
| JP | 7-218889 | 8/1995 |
| JP | 10-108857 | 4/1998 |

\* cited by examiner

OTHER PUBLICATIONS

McNichols and Cote, OPtical glucose sensing in biologocal fluids, Journal of Biomedical Optics, Jan. 2000, vol. 5. No. 1.*

*Primary Examiner*—Layla G. Lauchman
(74) *Attorney, Agent, or Firm*—Finnegan, Henderson, Farabow, Garrett & Dunner, L.L.P.

(57) ABSTRACT

To measure the concentration of an optically active substance in a solution without contacting the solution, the concentration measuring apparatus of the present invention includes: a light source for outputting linearly polarized light; a light intensity detecting element disposed opposite the light source with a sample placed therebetween; an optically active liquid crystal element placed between the light source and the light intensity detection circuit; a control circuit which controls the voltage to be applied to the optically active liquid crystal element so that an output value from the light intensity detecting element will in effect take an extreme value; and a concentration computing circuit for computing the concentration of an optically active substance in the sample, based on an output from the control circuit.

10 Claims, 16 Drawing Sheets

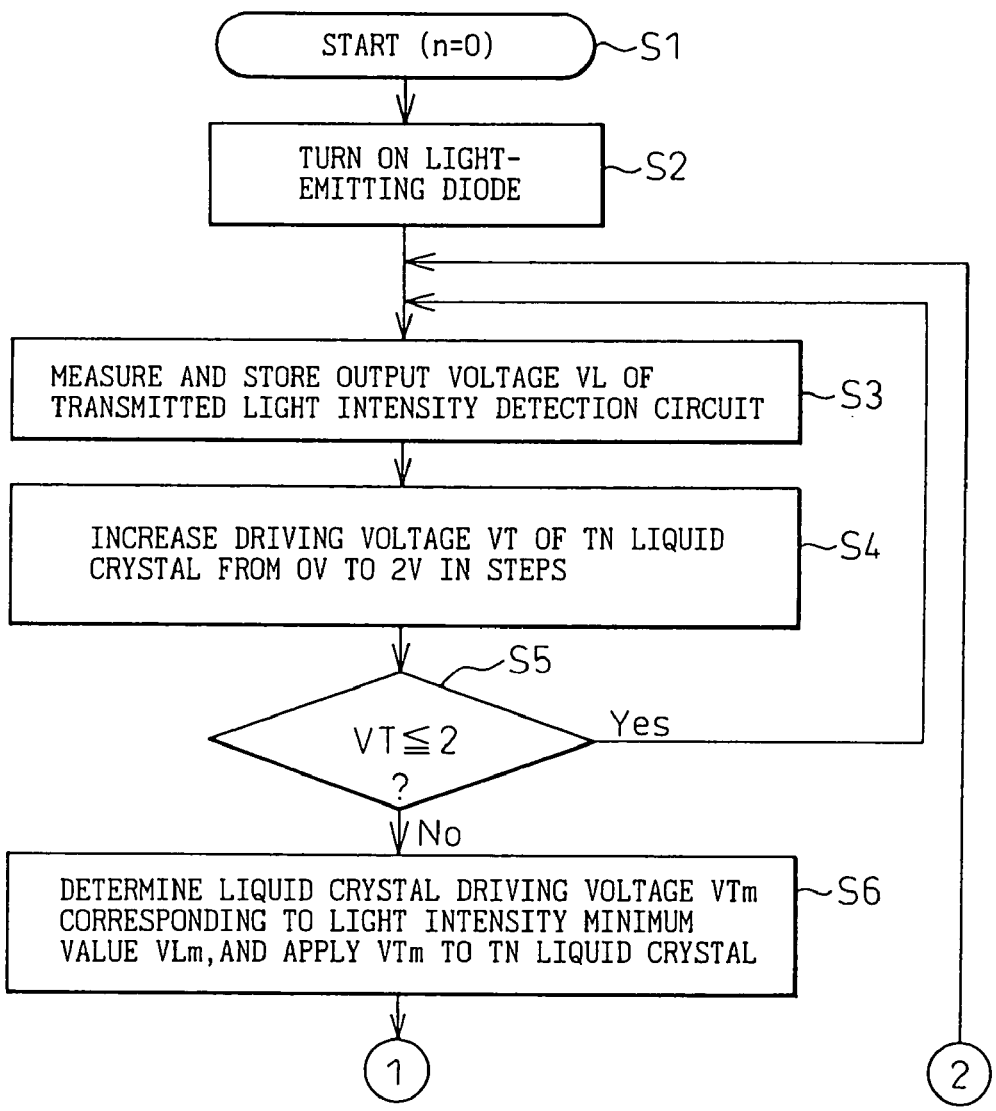

CONCENTRATION MEASURING INSTRUMENT

TECHNICAL FIELD

The present invention relates to a technology for measuring the concentration of an optically active substance dissolved in a solution, without using any mechanical moving devices and relying only on a purely electronic control method using an electronically-controllable, optical rotation control element.

The invention achieves a system for safe measurement of blood sugar concentration, management of the measured concentration, and notification of an alarm condition, wherein the system measures the concentration of blood sugar in a stable and non-harming way over an extended period of time, ideally by noninvasively measuring the blood sugar concentration in a human body or optically measuring the blood sugar concentration in urine in a non-contacting manner, or by using a linearly polarized light emitting element and a compact liquid-crystal, low-voltage, low-power consumption type optical rotation angle detecting element, both implanted in a human body.

In particular, for people with diabetes who need to manage their blood sugar levels in their daily lives, the invention provides a support tool to assist their social activities by achieving a system for issuing an alarm in an audible or visual manner or for automatically administering insulin or glucose as an emergency and temporary treatment when it could be expected that a serious effect to the human body would otherwise result. If a noninvasive blood sugar monitor is achieved, social activities free from blood taking can be ensured, especially for potential diabetics who account for nearly 10% of the population, and a useful health care apparatus can thus be provided.

PRIOR ART

In the prior art, to detect sugar concentration in an liquid solution, linearly polarized light is irradiated into the solution and, while changing the angle of rotation of a linear polarizer placed on an analyzer, {Angle of optical rotation/Light path length} is measured, and the sugar concentration is computed from the measured value. However, this method of measuring the angle of optical rotation in a solution, well known for the measurement of blood sugar concentration, requires taking a relatively large amount of blood sample from a human subject, and thus involves the pain of blood taking as well as a risk of potential infection.

To alleviate the pain and the risk, blood testing that only requires taking a trace amount of blood, and that uses an enzyme sensor, is already practiced to a certain extent on an everyday life level in the United States. However, this too is a skin invasive method that requires pricking the skin for blood taking, and therefore involves a risk of potential infection. Such invasive blood sugar measurement requires that the patient always carry antiseptic cotton so that the skin can be disinfected before taking blood. Furthermore, the psychological burden of the patient increases when he has to disinfect the skin and take blood in the presence of other people.

Apart from the above method, a noninvasive measurement method that places a warm heater on the skin to cause localized sweating and analyzes the constituents of the sweat has been proposed and practiced in certain areas. However, such a sweat-inducing heater requires power for heating and, if the heater is to be incorporated into a portable apparatus, the user may find the replacement of battery cells troublesome. Furthermore, there can arise the problem of skin burning by heating, and there can also occur cases where the measurement cannot be made because of a contact failure between the skin and the sweat-inducing heater. In fact, in the case of a wristwatch-type heater, the degree to which the wristband is tightened changes greatly from person to person, and hence, the degree of contact between the skin and the heater varies significantly among persons. As a result, when using a sugar concentration sensing wristwatch that requires adequate contact with the skin, a contact failure between the skin and the heater frequently occurs, depending on the user. For these and other reasons, it is extremely difficult to achieve safe and automatic real time monitoring of blood sugar concentration during social activities.

If a compact, low power consumption implantable blood sugar detector can be achieved that can be used over an extended period of time without replacing parts, this will provide a useful means even if it is not a noninvasive sugar concentration measuring apparatus. In this case also, an insulating structure between the human body and the measuring apparatus must be provided so that the measuring probe can stay within the body without affecting the blood.

SUMMARY OF THE INVENTION

An object of the invention is to achieve a noninvasive blood sugar monitoring apparatus that measures sugar concentration in human blood without taking a blood sample. To achieve this, sugar concentration must be computed by measuring the light transmittance in a human body without using any moving parts.

There has already been proposed a method for estimating blood sugar concentration by utilizing the property that the wavelength dependence of the transmittance of light of a particular wavelength in a human body changes with sugar concentration; however, it is difficult to detect the sugar concentration with high accuracy from human blood containing various kinds of constituents, and a practical noninvasive blood monitor has not been successfully implemented as yet. The degree of symptoms that the patient experiencing a low blood sugar level can aware may be weak, depending on the condition. Accordingly, in a situation where the patient himself is not able to notice the symptom, it is not possible to measure the blood sugar level at a proper time, and this threatens his life. To measure the blood sugar level even when the patient himself does not notice any symptom, automatic measurement under control of a clock is the only method available, but there is no means for providing a relief measure when the measurement failed.

If a noninvasive blood monitor is achieved, blood sugar can be measured under control of a clock, and the result can be fed back to the patient. To provide for the case where sugar or insulin cannot be administered to the patient in time, an automatic drug administering device can be used in combination with the automatic blood sugar measuring apparatus so that a safe amount of sugar or insulin can be automatically administered as a relief measure to prevent the patient from becoming unconscious.

The above apparatus facilitates the social activities of diabetics and potential diabetics. Even if the noninvasive blood sugar measurement thus taken contains a certain degree of error, providing warning to the patient before an accident occurs due to the blood sugar dropping below the normal level offers an advantage if it does not cause real harm. In social activity support applications, unlike the case of a precision blood sugar measuring apparatus for diagnosis or scientific analysis, a simple and easy-to-use blood sugar predictive measurement system that tolerates a finite degree of error is strongly needed. There is thus a need in society to provide a portable and handy noninvasive blood sugar concentration estimating apparatus.

The point of the configuration of the present invention is the electro-optical modulation of optical rotation by a twisted nematic liquid crystal element. In theory, sugar concentration can be measured by combining this liquid crystal element with a linear polarizer and a light receiving element. If an electro-optical phase modulating element constructed from a parallel aligned liquid crystal element is added to the above combination, and the amount of light is measured by converting elliptically polarized light into linearly polarized light, the accuracy of the optical rotation measurement further increases. More specifically, linearly polarized light is irradiated into an optically active sample, elliptically polarized light emerging from the sample is compensated for by the electro-optical optical rotation modulating element constructed from a twisted nematic liquid crystal element, the elliptically polarized light is converted back into the linearly polarized light by the electro-optical phase modulating element, an extreme value of detected light intensity is read, the drive voltages of the twisted nematic liquid crystal element and the phase modulating parallel aligned liquid crystal element are feedback-controlled, and the concentration of an optically active substance in the solution is computed by estimation from the electrical control voltage.

To improve the signal-to-noise ratio (hereinafter abbreviated S/N), the measurement of the transmitted light intensity and the measurement of the optical rotation are performed in parallel or in sequence within a short time, and the concentration of blood sugar, for example, is estimated from the predefined relationship between the value of the optical rotation and the light intensity within the sugar concentration measuring wavelength range. To prevent S/N degradation due to external light, it will be effective to also use a wavelength selective filter corresponding to the wavelength of the measuring light or to perform coded modulation in time-series fashion, thereby applying filtering appropriate to the code to the electrical signal output corresponding to the detected light, and thus measuring the blood sugar concentration by reducing the effects of external disturbing light.

In a specific example, a laser diode capable of emitting linearly polarized light or a combination of a light-emitting diode and a linear polarizer is used as the light source and, using a combination of the twisted nematic liquid crystal element for controlling the angle of optical rotation and the parallel aligned liquid crystal element for controlling the phase difference between the two components of birefringent light, automatic control is performed so that the angle of optical rotation produced by the sample is corrected in the reverse direction to roll back the angle of rotation and restore the original linearly polarized light, and the sugar concentration in blood is estimated from the value of the liquid crystal driving voltage need for the above rotation angle control.

In a modified example of the above principle, the linearly polarized light is rotated in advance by the rotation angle controlling liquid crystal element in a direction opposite to the direction of the rotation to be produced by the sample; here, a voltage is applied to the rotation angle controlling liquid crystal element so that the angle of polarization of the light will return to the original angle of polarization when the light is passed through the sample. In the case of elliptically polarized light, the elliptically polarized light is converted by the phase modulating liquid crystal element back to the linearly polarized light, to improve the S/N ratio.

BRIEF DESCRIPTION OF THE DRAWINGS

FIG. 16A is a diagram showing the first half of a flowchart illustrating a procedure for measuring sugar concentration in a solution by using the concentration measuring apparatus shown in FIG. 1.

EMBODIMENTS

Figure 1:
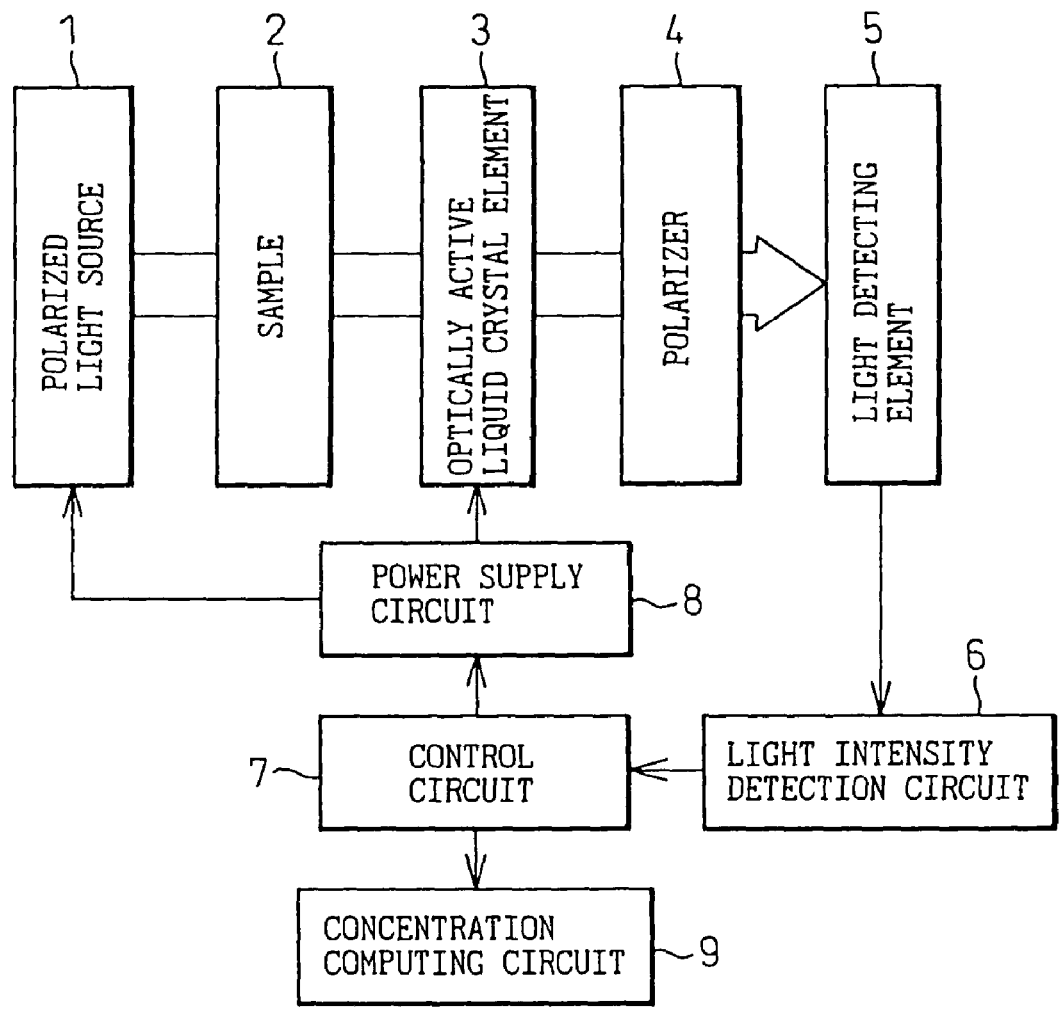
FIG. 1 is a block diagram showing the configuration of a concentration measuring apparatus according to a first embodiment of the present invention.

FIG. 1 is a block diagram showing the configuration of a concentration measuring apparatus according to a first embodiment of the present invention. In the figure, reference numeral 1 is a light source which emits linearly polarized light and is constructed, for example, from a laser diode or the like. Reference numeral 2 is a sample for which the concentration of an optically active substance in a solution is to be measured by the apparatus of the present invention. If the sample is blood, and the optically active substance is sugar, then the analyte is dextroglucose. Reference numeral 3 is an optically active liquid crystal element, which is formed from a twisted nematic liquid crystal.

When using the concentration measuring apparatus of the invention as an optical rotation compensating type apparatus, a left-hand twisted nematic liquid crystal element is used, and when using it as an optical rotation adding type apparatus, a right-handed twisted nematic liquid crystal element is used. Reference numeral 4 is a linear polarizer, 5 is a light detecting element constructed from a photodiode or a light receiving element, and 6 is a light intensity detection circuit. Further, reference numeral 7 is a control circuit which, based on the detection value from the light detecting element 5, determines the voltage to be applied to the optically active liquid crystal element 3. Reference numeral 8 is a power supply circuit which, based on the output of the control circuit, supplies the necessary voltage to the optically active liquid crystal element 3 as well as the voltage necessary to drive the light source 1. Reference numeral 9 is a concentration computing circuit which, based on the control output of the control circuit 7, computes the concentration of the optically active substance in a solution. When using a reverse-biased photodiode as the light detecting element, the power supply circuit 8 may be configured to supply the reverse-biasing voltage.

The operation of the thus configured concentration measuring apparatus will be described below.

As the molecules of the optically active substance are oriented in a random manner in the sample 2, the polarization plane of the linearly polarized light emitted from the light source 1 is rotated while passing through the sample 2, and emerges as elliptically polarized light. Accordingly, when the twisted nematic liquid crystal element 3 is placed which produces an optical rotation in a direction opposite to the direction of rotation of the light emerging from the sample, the elliptically polarized light passing through the liquid crystal element 3 is modulated in a direction that rolls back the plane of polarization. Here, consider the situation where pure water is introduced as the sample 2, and a voltage, for example, 10 V, is applied to the twisted nematic liquid crystal element 3 (a condition that does not produce optical rotation); in this condition, if the linear polarizer 4 is arranged with its polarization plane oriented at right angles to the polarization plane of the light source 1, as the polarized light from the light source reaches the polarizer 4 without being modulated by the sample, the light is blocked by the polarizer 4. As a result, the output of the light detecting element 5 exhibits the lowest value.

Next, when a dextrorotatory D-glucose solution is introduced as the sample 2 to replace the pure water, the linearly polarized light from the light source is rotated to the right by the dextrorotatory power of the sample 2, so that the light passes through the polarizer 4 and emerges as bright light. When the voltage being applied to the left-hand twisted liquid crystal element 3 is lowered, the rotatory power of the liquid crystal element 3 is restored, which works to compensate for the optical rotation produced by the D-glucose; as a result, the light emerging from the polarizer 4 darkens again. When the voltage to be applied to the liquid crystal element 3 is adjusted for the least emergent light, the applied voltage for the darkest light becomes a function of the concentration of the D-glucose.

In the above configuration, consider the case in which the liquid crystal element is a right-hand 90-degree twisted nematic liquid crystal element and the applied voltage is 0 V, the sample here being pure water. As the polarizer is oriented at 90 degrees to the polarization plane of the light source 1, the output intensity of the light detecting element 5 represents the brightest condition because the light was rotated through 90 degrees by the rotatory power of the twisted nematic liquid crystal element 3. When the pure water is replaced by a dextrorotatory D-glucose solution, the output intensity of the light detecting element 5 decreases because of the dextrorotatory nature of the solution. When the voltage being applied to the 90-degree twisted nematic liquid crystal element 3 is increased, the optical rotation produced by the liquid crystal element 3 decreases, and when the voltage reaches the point where the total of the angle of optical rotation produced by the dextrorotatory solution and the angle of optical rotation produced by the liquid crystal element is equal to 90 degrees, the light becomes the brightest. Detecting the darkest condition can reduce design constraints compared with the case of detecting the brightest condition, because the circuit saturation problem can then be avoided; therefore, the polarizer is set at a position rotated 90 degrees. In that case, when the voltage applied to the 90-degree twisted nematic liquid crystal element is 0, and the sample is pure water, the darkest condition is produced, and the applied voltage increases as the sugar concentration in the D-glucose solution increases. However, as the light which passes through the sample emerges as elliptically polarized light, and the light which passes through the twisted nematic liquid crystal element also emerges as elliptically polarized light, a completely dark condition cannot be obtained, and this can cause an error in the sugar concentration measurement. Furthermore, as the applied voltage for the darkest condition is determined by obtaining the variable (=applied voltage) that minimizes the gentle function (=received light intensity), the applied voltage for the darkest condition must be determined by using a technique that approximates an easily analyzable function from many measured values in the neighborhood of the darkest point and computes the applied voltage that minimizes the approximated function.

Figure 2:
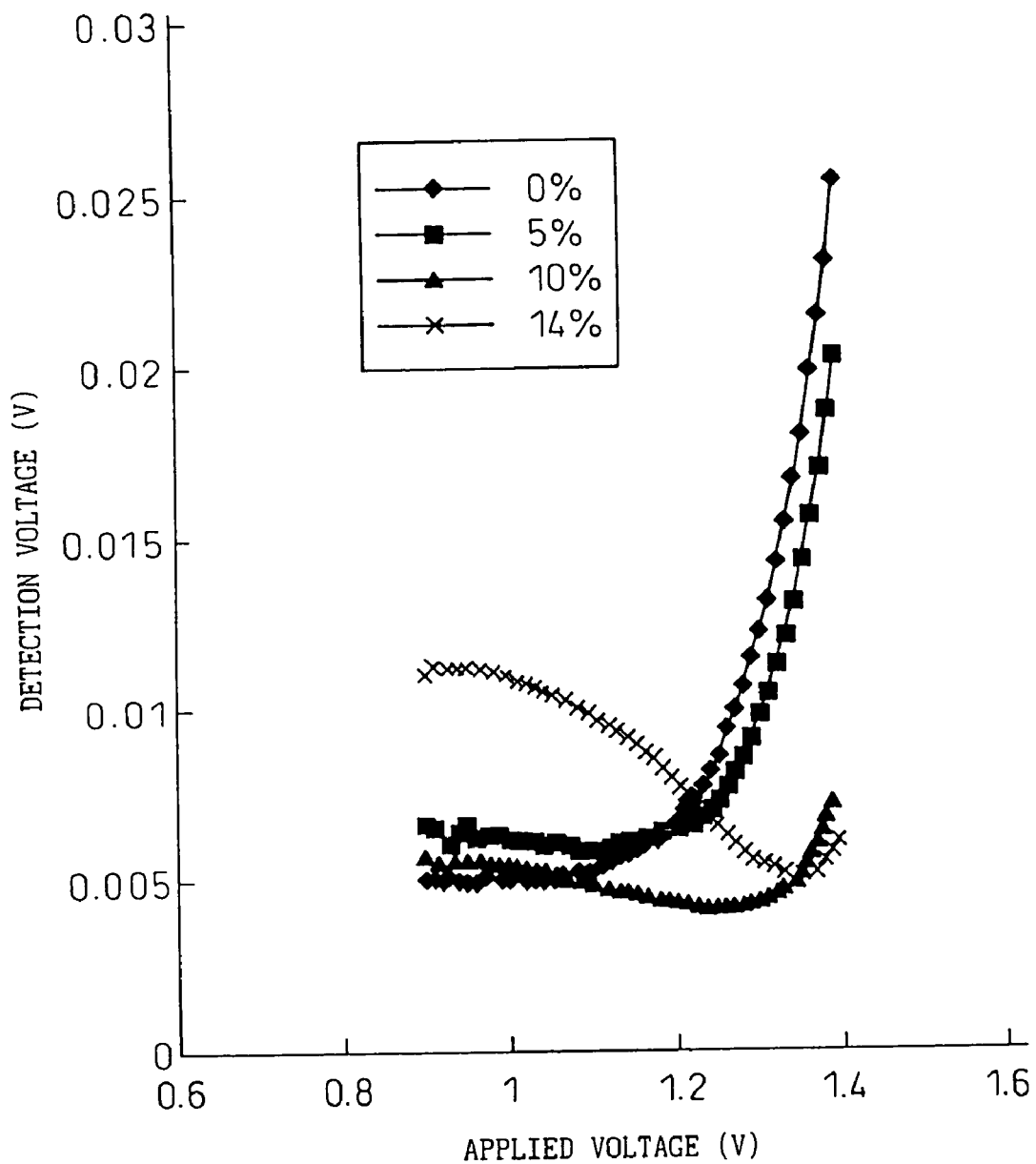
FIG. 2 is a graph showing the relationship between an applied voltage to an optically active liquid crystal element and an output of a light detecting element.
Figure 3:
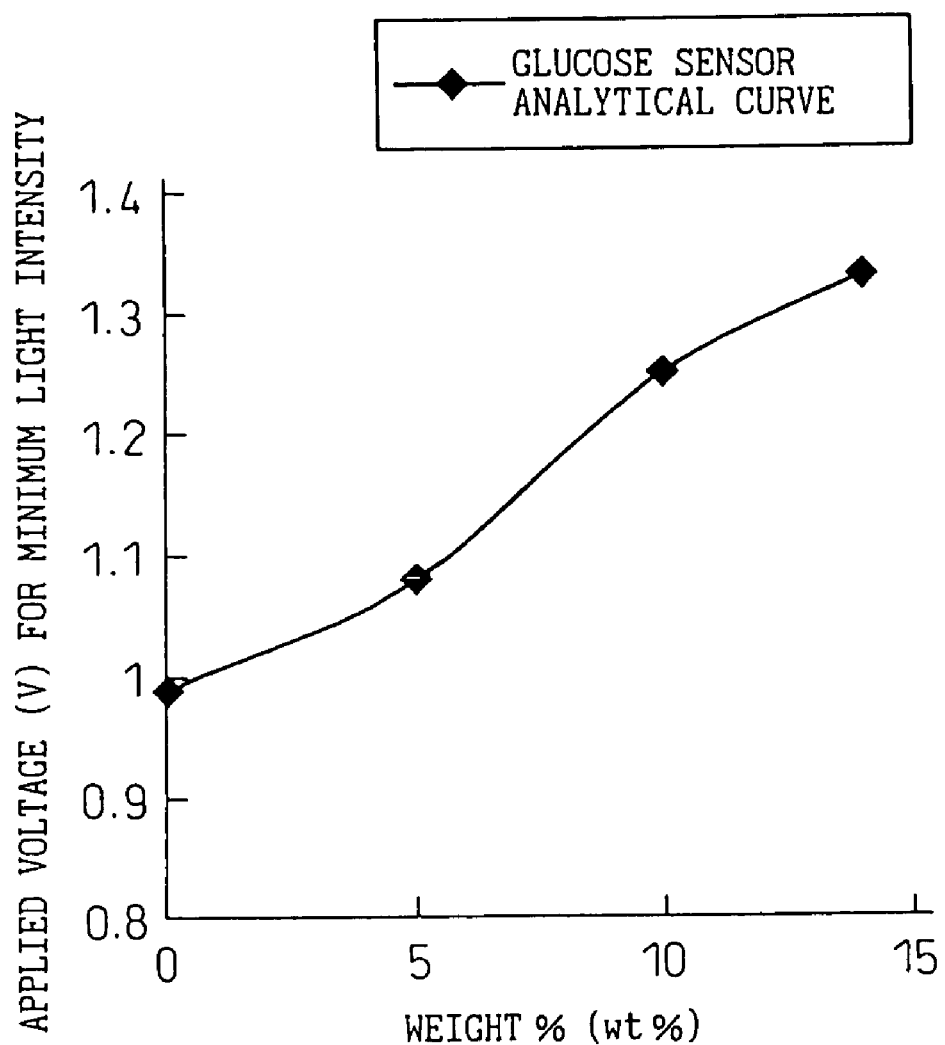
FIG. 3 is a graph showing the relationship between sugar concentration and applied voltage.

Using the above configuration, the right-hand 90-degree twisted nematic liquid crystal element was used in combination with a D-glucose analyte solution, and the linear polarizer 4 was arranged with its plane oriented so as to produce the darkest condition with a pure water sample; then, the voltage applied to the twisted nematic liquid crystal element was varied so as to provide such an angle that produced the darkest condition with the pure water sample, without using a phase-correcting alignment liquid crystal element. The actually measured data in the above arrangement are shown in FIG. 2, and the analytical curve derived from the data is shown in FIG. 3. In the glucose sensor characteristics shown in FIG. 2, the abscissa represents the voltage (V) applied to the twisted nematic liquid crystal element, and the ordinate represents the output (V) of the light intensity detection circuit. In the glucose sensor analytical curve shown in FIG. 3, the abscissa represents the sugar concentration expressed as percent by weight, and the ordinate represents the liquid crystal driving voltage (V) that minimizes the light intensity. From this graph, it can be seen that the sugar concentration in the solution can be computed by the apparatus of FIG. 1 by detecting the applied voltage to the optically active liquid crystal element 3 that minimizes the output of the light detecting element 5. The concentration computing circuit 9 in FIG. 1 is a circuit which, based on the prestored data such as shown in FIG. 3, obtains the concentration of the optically active substance in a solution from the applied voltage to the optically active liquid crystal element 3 determined by the control circuit 7.

In the embodiment shown in FIG. 1, if the optically active liquid crystal element 3 is placed between the light source 1 and the sample 2, the concentration can be measured in the same manner as described above.

Figure 4:
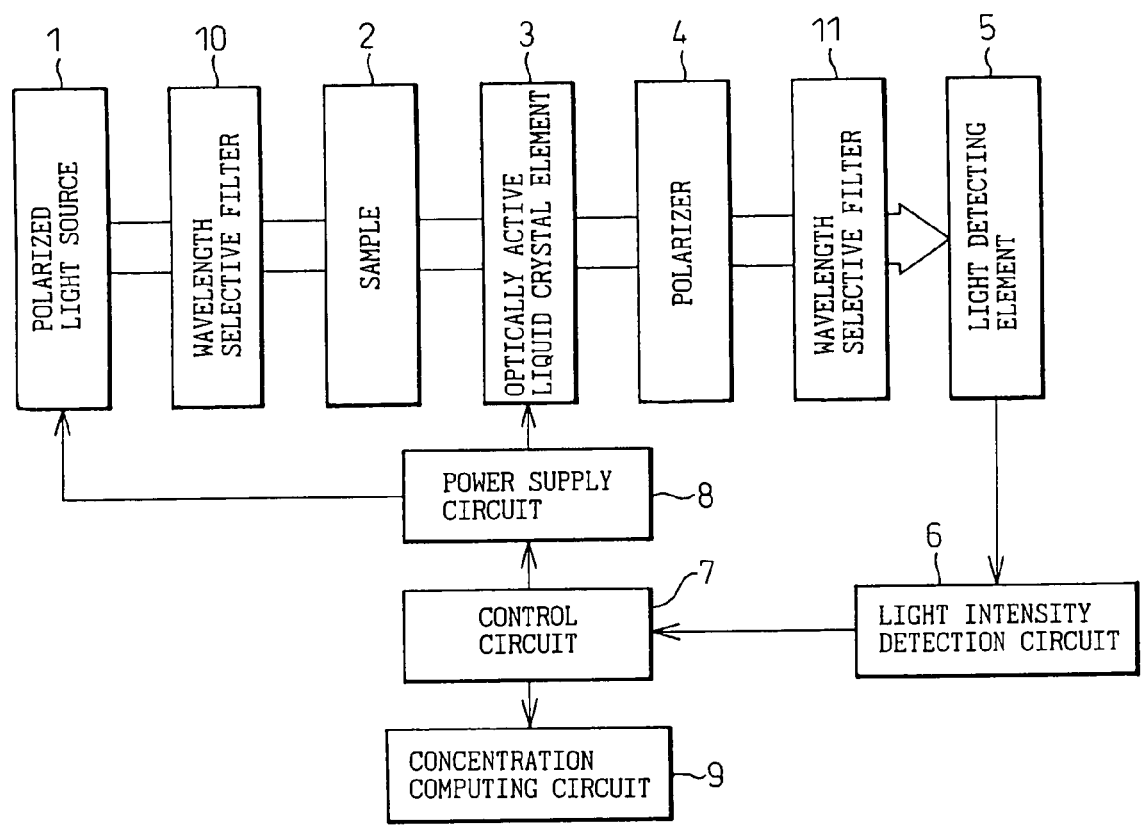
FIG. 4 is a block diagram showing the configuration of a concentration measuring apparatus according to a second embodiment of the present invention.

FIG. 4 is a block diagram showing the configuration of a concentration measuring apparatus according to a second embodiment of the present invention. This embodiment differs from the configuration shown in FIG. 1 by the inclusion of a light wavelength selective filter 10 on the exit side of the light source 1 and a second wavelength selective filter 11, placed between the polarizer 4 and the light detecting element 5, for transmitting therethrough only the light passed through the wavelength selective filter 10. With this arrangement, as only the light of a particular wavelength is used for the measurement, the signal-to-noise (S/N) ratio of the measurement can be improved.

Figure 5:
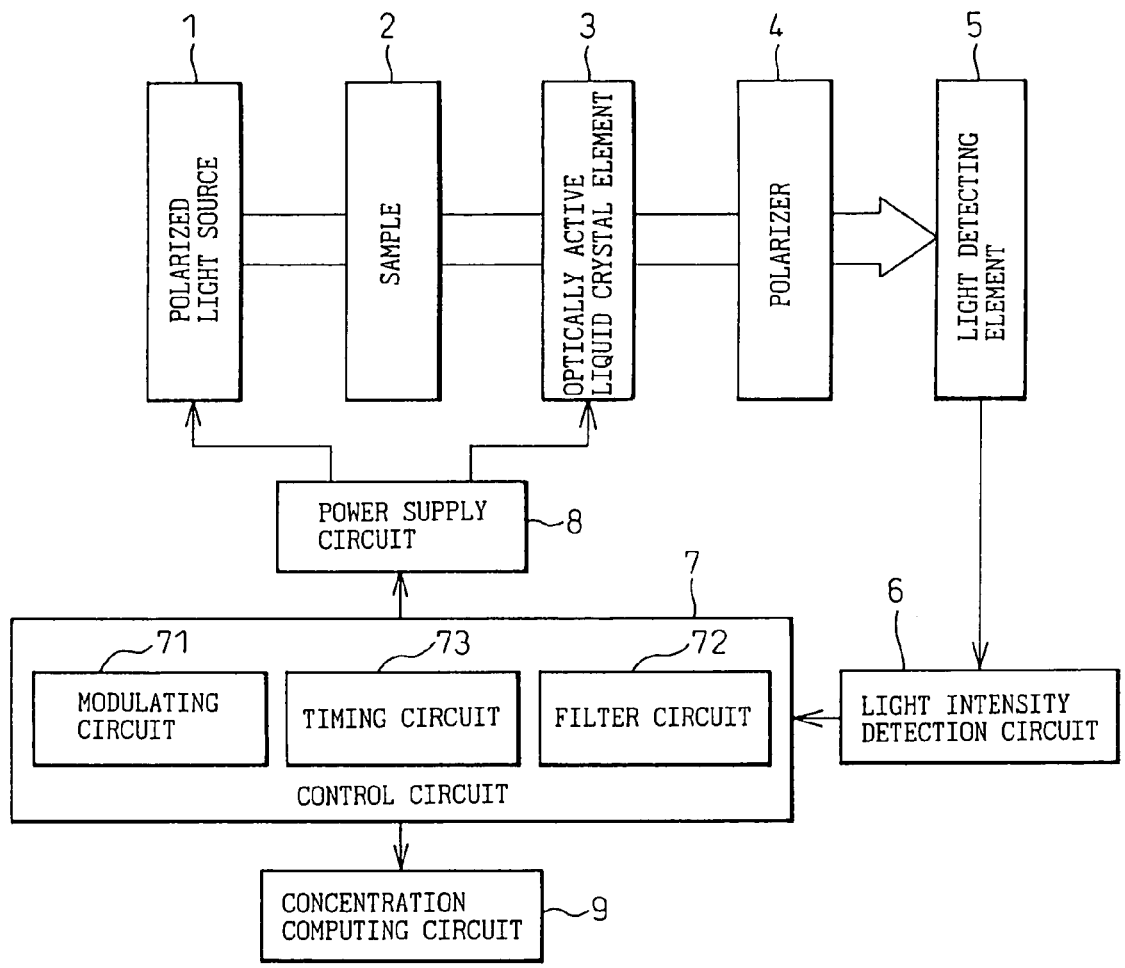
FIG. 5 is a block diagram showing the configuration of a concentration measuring apparatus according to a third embodiment of the present invention.

FIG. 5 is a block diagram showing the configuration of a concentration measuring apparatus according to a third embodiment of the present invention. This embodiment differs from the configuration shown in FIG. 1 in that the control circuit 7 includes a modulating circuit 71 for modulating the light emitting intensity of the light source 1 with a particular code or frequency, a filter circuit 72 for extracting a modulated signal contained in the electrical output signal of the light intensity detecting element 5, and a timing circuit 73 for generating timing common to the respective circuits. With this configuration, as only the optical signal from the modulated light source can be separated out by the filter circuit 72 for detection, the S/N ratio of the signal improves.

Figure 6:
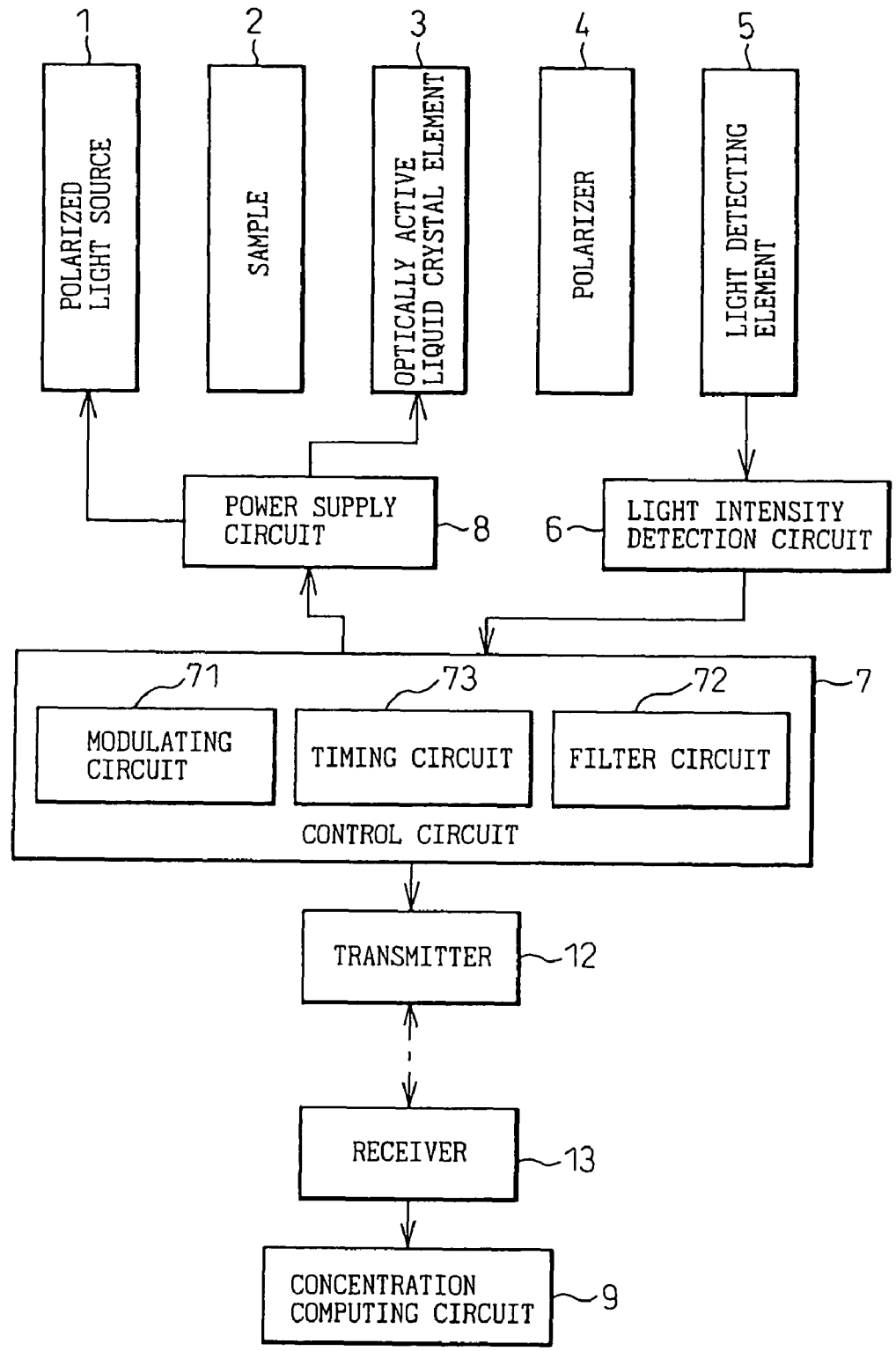
FIG. 6 is a block diagram showing the configuration of a concentration measuring apparatus according to a fourth embodiment of the present invention.

FIG. 6 is a block diagram showing the configuration of a concentration measuring apparatus according to a fourth embodiment of the present invention. This embodiment differs from the configuration shown in FIG. 5 in that a transmitter 12 and a receiver 13 are provided so as to be able to remotely control the sensor section comprising the light source 1, optically active liquid crystal element 3, light detecting element 5, light intensity detection circuit 6, control circuit 7, and power supply circuit 8. This configuration is suitable for applications where the concentration measuring apparatus of the invention is worn on a human body or implanted in the body. That is, the light source 1, optically active liquid crystal element 3, polarizer 4, light detecting element 5, light intensity detection circuit 6, control circuit 7, power supply circuit 8, and transmitter 12 may be implanted in the human body, in which case the output of the control circuit 7 is transmitted via the transmitter 12 and the receiver 13 to the control and analysis apparatus external to the body. In this way, by minimizing the size of the part to be implanted in the body, the burden on the human body can be alleviated. In FIG. 6, when the transmitter 12 and the receiver 13 are constructed as a single transceiver unit, the control circuit 7 can be placed outside the human body.

Figure 7:
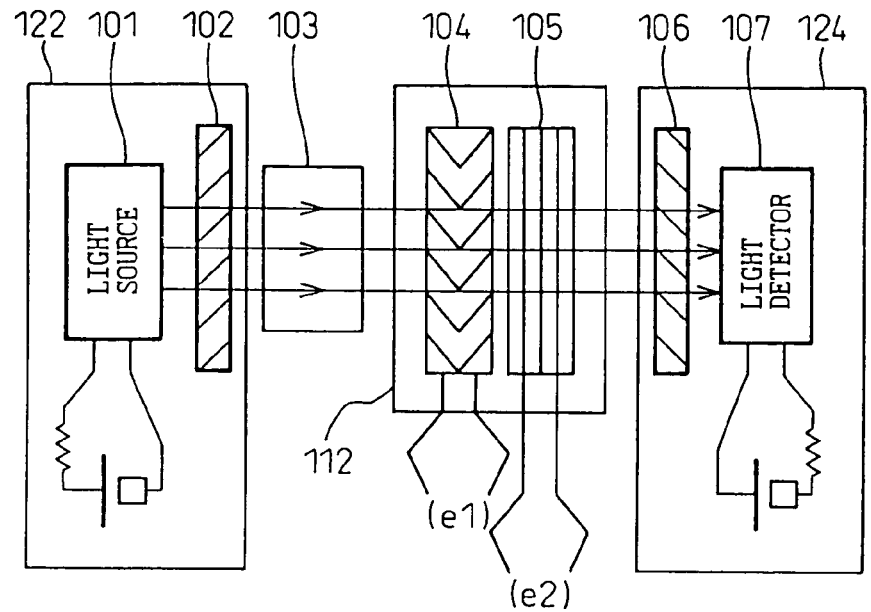
FIG. 7 is a block diagram showing the configuration of a concentration measuring apparatus according to a fifth embodiment of the present invention.

FIG. 7 is a functional block diagram for explaining the configuration of a fifth embodiment of the present invention. Here, reference numeral 122 is a linearly polarized light source means. This light source means can be constructed, for example, by combining a light-emitting diode with a linear polarizer 102. Alternatively, a laser diode capable of emitting linearly polarized light may be used as the light source 101. In the latter case, the linear polarizer 102 can be omitted. Reference numeral 103 is an optically active sample, 112 is an electro-optical optical rotation modulating means for compensating for the optical rotation given by the optically active sample, and 124 is a linearly polarized light intensity detecting means. If the sample 103 is human blood or a solution containing light-scattering particles, disturbance of the polarization or scattering of light occurs. Further, in the case of a body fluid, light transmittance varies as a function of time.

The optical rotation compensating means is a means that performs a modulation for compensating for the angle of optical rotation and a phase compensating modulation for converting elliptically polarized light into linearly polarized light, in order that the light elliptically polarized by being subjected to the rotation angle modulation and birefringence in the sample can be detected with high S/N ratio (signal-to-noise ratio) by the light intensity detecting means 124.

For the optical rotation modulation, a liquid crystal element is used that exhibits a twisted structure in which the liquid crystal molecules are oriented in twisted fashion. In the twisted nematic liquid crystal element, the polarized component that matches the orientation direction of the substrate is allowed to enter and is rotated through an angle equal to the twist angle. When a high voltage is applied, the optical rotatory power decreases, and the angle of optical rotation changes. Utilizing this property, the angle of optical rotation is adjusted electrically. For the phase modulation, a parallel aligned liquid crystal element is used. The orientation direction of the substrate is set at about 45 degrees with respect to the major axis of the elliptically polarized light, and the incident elliptically polarized is converted into linearly polarized light by adjusting the applied voltage to the liquid crystal element, and thereby adjusting the phase difference between the ordinary light and extraordinary light with the phase difference produced by the liquid crystal element.

As, in the optically active liquid crystal element, not the optical rotation but elliptical polarization also occurs, as previously described, the elliptically polarized light is converted back to the linearly polarized light by using the parallel aligned liquid crystal element provided to adjust the phase difference between the two components of birefringent light.

The linearly polarized light intensity detecting means 124 is constructed from a combination of a linear polarizer 106 and a light intensity detecting element 107. Light which has passed through the linear polarizer enters the light detecting element 107; with the light detecting element 107 which is independent of optical rotation, an output proportional to the intensity of the linearly polarized light can be obtained. For the light detecting element, use can be made of a reverse-biased silicon semiconductor PN junction element, a phototransistor element, a cadmium sulfide photoconductive element, or the like. The linear polarizer can be constructed using an inexpensive, commercially available 50% absorption-type linear polarizer.

The above system, in which the optical rotation modulation applied by the sample is compensated for by using the optical rotation modulating liquid crystal element and the phase modulating liquid crystal element, can be implemented as a system that uses a zero method in which the leakage light of detection light is detected and the compensation is performed so as to minimize the leakage light, or alternatively as a system that uses a maximum value tracking method in which the amount of light incident on the detecting element is detected and the compensation is performed so as to maximize the amount of incident light.

When a solid-state laser diode is used as the light source 101, the converging optics can be eliminated, and the structure can thus be simplified. The sample 103 is a human body part, such as a finger, an earlobe, or a portion of an arm, through which blood is flowing. The optical rotation control element 104 is an optical rotation controlling twisted liquid crystal element comprising a pair of transparent substrates disposed opposite each other and having transparent electrodes formed thereon, the substrates being treated to provide a low tilt angle close to an angle parallel to the substrates. The twist angle need not necessarily be set to 90 degrees, but can be set within a range from an angle approximately equal to the angle of optical rotation produced by the sample to about 360 degrees. When the voltage applied between the substrates is 0, the polarization plane of the light entering the liquid crystal element is rotated through an angle equal to the twist angle. When the angle of the polarization plane of the entering light does not match the angle of the liquid crystal molecular orientation, optical rotation modulation and elliptical polarization occur at the same time because the component of light that matches the molecular orientation and the component of light orthogonal to it propagate at different velocities. When the applied voltage is significantly higher than the threshold of the liquid crystal element, the liquid crystal molecules in the liquid crystal element are aligned perpendicularly to the substrates, so that the rotatory power is lost and the angle of optical rotation becomes 0. When the applied voltage is in the vicinity of the threshold, both the angle of optical rotation and the degree of elliptical polarization change according to the applied voltage.

The parallel aligned liquid crystal element 105 is a liquid crystal element constructed by forming transparent electrodes on a pair of transparent substrates treated for alignment and arranged opposite each other with their alignment directions pointing in the same direction, and by injecting a liquid crystal material to fill the gap between the substrates. When the applied voltage is 0, there arises a phase difference between the component of light parallel to the molecular orientation and the component of light orthogonal to it, and when a voltage higher than the threshold is applied between the transparent electrodes sandwiching the liquid crystal layer therebetween, the liquid crystal molecules are aligned perpendicularly to the substrates, so that the phase difference becomes 0. When the applied voltage in terms of RMS is in the vicinity of the threshold, the degree of the phase difference varies depending on the applied RMS voltage.

The RMS voltage applied to each liquid crystal element is adjusted so that the light rotated and elliptically polarized by passing through the sample 103 will be rotated back to its original orientation, i.e., the linearly polarized light, when passed through the optical rotation compensating element 104 and the phase control element 105. Depending on the configuration, the angle of optical rotation may be increased so as to provide an angle orthogonal to the polarization plane of the output light of the linearly polarized light source 122. The linear polarizer 106 is arranged with its plane oriented at right angles to the polarization plane of the light passed through the polarizer 102 and the optical rotation control element in the absence of an applied voltage so that the amount of transmitted light is a minimum when the sample 103 is removed.

One optical rotation measuring method is the zero method in which the photocurrent from the light detecting element 107 is converted to a voltage, and the optical rotation control element 104 and the phase control element 105 are controlled through negative feedback of the RMS (Rout-mean-square value or effective value) voltage for driving each control element so that the output voltage value becomes a minimum.

In another method, the polarizers 102 and 106 are arranged with their polarization planes oriented parallel to each other so that the amount of transmitted light is maximum when the sample 103 is removed, and the voltages to be applied to the phase modulating liquid crystal element and the optical rotation modulating liquid crystal element are adjusted through feedback control of the RMS voltages for driving the phase control element 105 and the optical rotation control element 104 so that the output current of the light detecting element 107 becomes a maximum for measurement when the sample is introduced.

The first method has the advantage of being able to achieve a highly accurate measurement when there is relatively little external disturbing light, while the second method has the advantage of being able to perform control using a large signal voltage from the electrical circuit when the amount of light from the light source is small.

In the configuration where the angle of optical rotation produced by the sample is advanced by 90 degrees by the optical rotation modulating liquid crystal element instead of turning it back to the original orientation, by rotating the polarization plane of the analyzer through 90 degrees the zero method or the maximum value tracking method earlier described can be used.

The effects of external disturbing light can be eliminated by varying the amount of light from the light source as a function of time and amplifying the resulting difference. The effects of external disturbing light include a saturation of the light detecting element 107 or a saturation resulting from an excessively large input to the differential amplifier circuit, and from the standpoint of increasing the S/N ratio, it will be effective to increase the power of the light source 101, within a range that does not cause a saturation, so that the light will not be buried under external light.

In a configuration where the differential amplifier circuit is operated in a time division fashion, the voltage level of the light detection signal obtained when the power of the light source is set to a small value L0 is stored as S0 in a sample-and-hold circuit, and the voltage level of the light detection signal obtained when the power of the light source is increased to L1 is denoted by S1; then, when the signals S1 and S0 are coupled to the two differential input of the differential amplifier circuit, the difference is detected and amplified. With this method, the effects of the external disturbing light can be alleviated.

Further, as the detected signal component can be converted to AC by modulating it over time, an AC amplifier circuit can be utilized, and the technique of a lock-in amplifier having a good S/N ratio that performs frequency filtering can be used to allow only the frequency of the amplified signal near the time modulating signal component to pass through, thereby detecting the signal synchronously with the frequency.

As the blood in a living human body is pulsating, from the standpoint of increasing the S/N ratio of sugar detection it is effective to extract pulsating components from the time variation of the detected light intensity and to sample the sugar concentration synchronously with the pulsation frequency. The various methods described above are one embodiment of bio-signal filtering. For stable and low-power operation of the above system, it is effective to use low-power oscillation by a crystal oscillator and signal processing by a CMOS integrated circuit, in combination with a low-power display by a liquid crystal display device and an alarm indication by voice.

A modification can be made to the configuration of FIG. 7. For example, the optical rotation reverse compensating liquid crystal element 104 and the phase compensating liquid crystal element for converting the elliptically polarized light back to linearly polarized light may be placed before the sample 103.

Figure 8:
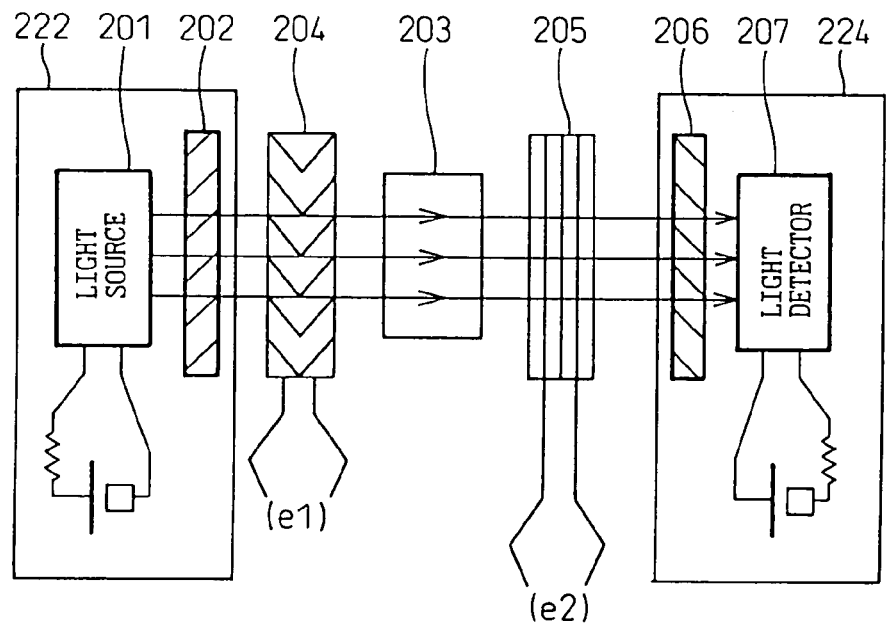
FIG. 8 is a block diagram showing the configuration of a concentration measuring apparatus according to a sixth embodiment of the present invention.

FIG. 8 is a block diagram showing the configuration of a concentration measuring apparatus according to a sixth embodiment of the present invention. Reference numeral 222 is a linearly polarized light source, 201 is a light-emitting element, and 202 is a linear polarizer which can be omitted if the light-emitting element 201 is a laser diode. Reference numeral 204 is an optical rotation control element; the orientation direction of the liquid crystal molecules in the optical rotation control element is aligned with the polarization plane of the linearly polarized light source. The output of the optical rotation control element 204 is linearly polarized light whose polarization plane is rotated through an angle equal to the twist angle when the applied voltage is 0; the angle of rotation of the polarization plane decreases as the applied voltage increases. The driving voltage of the optical rotation control element 204 is adjusted so that the angle of polarization plane rotation produced by the optical rotation control element 204 becomes equal in magnitude but opposite in sign to the angle of optical rotation produced by the sample 203. The polarization plane of the light passed through the optical rotation control element 204 and emerging from the sample 203 is corrected and oriented so as to contain the polarization plane of the light source 222 as well as the optical axis thereof, but the light is elliptically polarized. The elliptically polarized light can be adjusted by adjusting the driving voltage applied to the phase modulating element 205. The phase modulating element 205 is arranged with its plane oriented at 45 degrees relative to the polarization plane of the light source.

Figure 9:
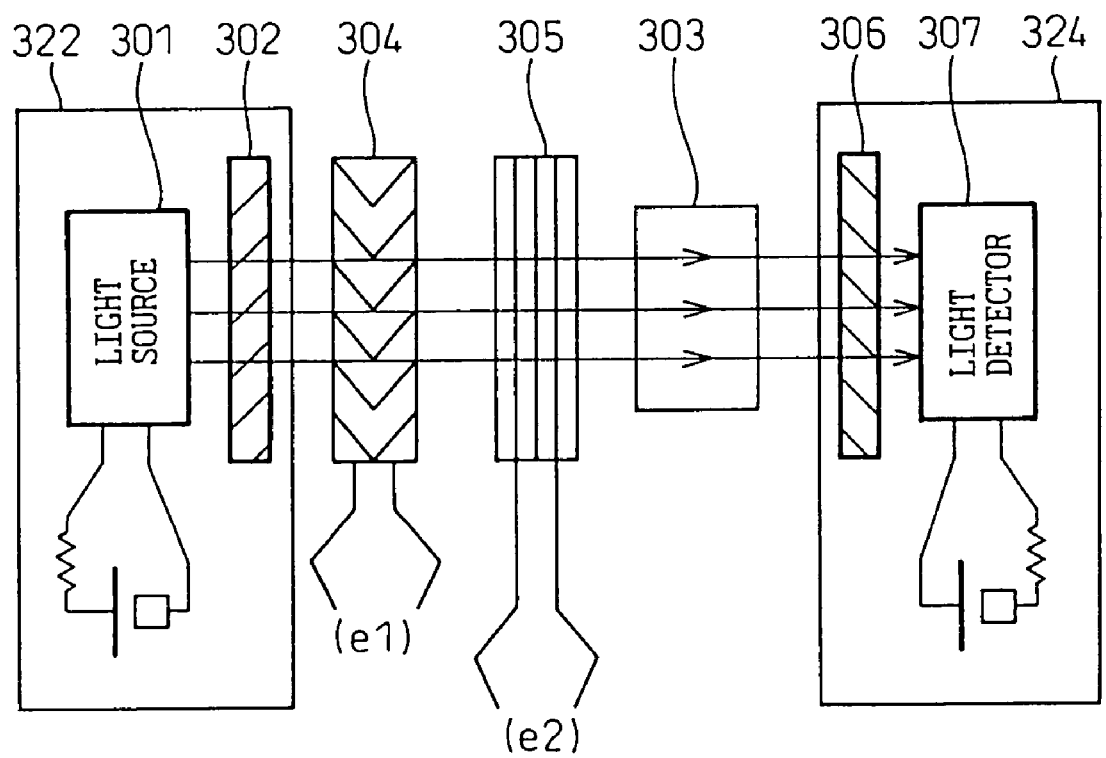
FIG. 9 is a block diagram showing the configuration of a concentration measuring apparatus according to a seventh embodiment of the present invention.

FIG. 9 is a block diagram showing the configuration of a concentration measuring apparatus according to a seventh embodiment of the present invention. Reference numeral 322 is a linearly polarized light source, 301 is a light-emitting element, and 302 is a linear polarizer which can be omitted if the light-emitting element 301 is a laser diode. Reference numeral 304 is an optical rotation control element; the orientation direction of the liquid crystal molecules in the optical rotation control element is aligned with the polarization plane of the linearly polarized light source. On the output side of the optical rotation control element 304 is placed a phase control element so that the linearly polarized light emerges as elliptically polarized light from the latter; here, the optical rotation control element 304 and the phase control element 305 are controlled so that the light emerging from the sample 303 is close to linearly polarized light. The light elliptically polarized by passing through the two control elements is made close to linearly modulated light by passing through the sample 303, and the angle of optical rotation is detected. Reference numeral 306 is a linear polarizer, 307 is a light detecting element, and 324 is a linearly polarized light detecting means. The driving voltage of the optical rotation control element 304 is adjusted so that the angle of polarization plane rotation produced by the optical rotation control element 304 becomes equal in magnitude but opposite in sign to the angle of optical rotation produced by the sample 303. The polarization plane of the light passed through the optical rotation control element 304 and emerging from the sample 303 is corrected and oriented so as to contain the polarization plane of the light source 322 as well as the optical axis thereof, but the light is elliptically polarized. The elliptically polarized light can be adjusted to linearly polarized light by adjusting the driving voltage applied to the phase modulating element 305. The phase modulating element 305 is arranged with its plane oriented at 45 degrees relative to the polarization plane of the light source.

Figure 10A:
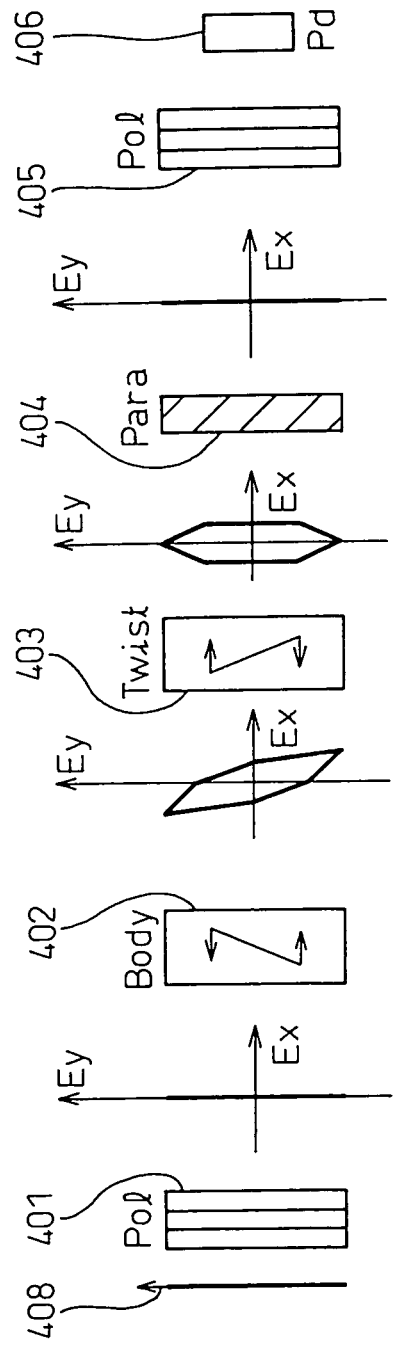
FIG. 10A is a diagram for explaining the operation of the concentration measuring apparatus according to the present invention.

Control of the polarized wavefront in the configurations shown in FIGS. 7 and 8 will be explained with reference to FIGS. 10A and 10B, respectively. In FIG. 10A, the output light 408 from the linearly polarized light source is passed through the linear polarizer 401 and enters the sample 402; then, in the optical rotation control element 403 on the exit side, the angle of the polarization plane of the light is compensated for and rotated back to the same orientation as the light source output light 408, and the resulting elliptically polarized light is converted back to linearly polarized light by a birefringence phase difference modulating element 404.

Figure 10B:
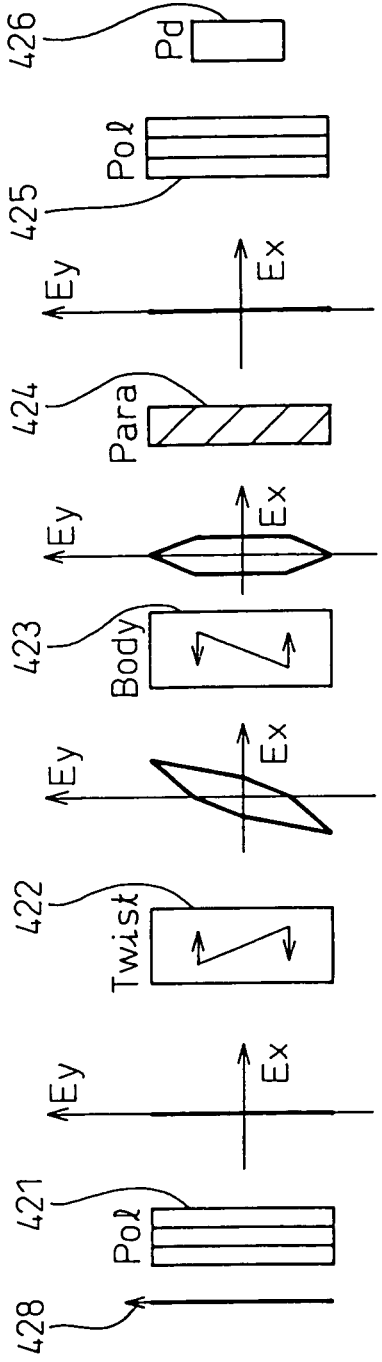
FIG. 10B is a diagram for explaining the operation of the concentration measuring apparatus according to the present invention.

In FIG. 10B, the output light 428 from the linearly polarized light source is passed through the linear polarizer 421 and enters the optical rotation control element 422 where the angle of the polarization plane is adjusted before entering the sample 423; as a result of the compensation, the plane of polarization is oriented in the same direction as that of the light source output light 428, and the resulting elliptically polarized light is corrected by a birefringence phase difference modulating element 424 into linearly polarized light which is then passed through the linear polarizer 425 and detected by the light detecting element 426 where the light intensity is detected.

An embodiment of a method for achieving a condition in which the optical rotation produced by the sample is automatically compensated for will be described with reference to the configuration of FIG. 8. The angle of optical rotation produced by the sample 203 is denoted by θ1, and the angle of optical rotation produced by the compensating element is represented by θ2.

It is assumed here that a right-handed optical rotation occurs as the concentration, x, of the optically active substance in the sample increases.

$\theta1(x) = a \cdot x$ ... $a$ is a constant.

Initially, x=0 (=concentration 0)

The angle of optical rotation, θ(v), produced by the optical rotation compensating element is a function of the driving voltage e1 of the optical rotation controlling liquid crystal element 204. The angle of optical rotation when e1=0 is denoted by θ0, which is expressed by the following equation.

$\theta2(e1) = \theta0 - b \cdot e1$ ... $b$ is a constant.

When the angle of optical rotation of the light passed through both the optical rotation compensating element 204 and the sample 203 is denoted by θs, then $\theta s = \theta2(e1) + \theta1(x) = \theta0 - b \cdot e1 + a \cdot x$ As for the output voltage Vdt of the light detecting means 224, the rotation position of the polarizer is chosen so as to enhance the control sensitivity and is set so that the amount of transmitted light becomes 0 when the optical rotation produced by the sample is 0. Accordingly, the initial position of the rotation angle of the polarizer 206 is {θ0+90 degrees}.

If x=0 and e1=0, the amount of light incident on the light detecting element 207 is 0, and the electrical output Vdt of the light detecting element 207 is therefore 0.

When the concentration, x, of the optically active sample increases, i.e., x>0, and the angle of optical rotation, θs, of the light passed through both the rotatory power compensating element 204 and the sample 203 becomes larger than θ0, the electrical output of the light detecting element 207 is then Vdt>0. The voltage e1 for driving the optical rotation controlling liquid crystal element 204 is created by amplifying Vdt, and a negative feedback is applied. When the value of e1 is gradually increased, the amount of change of the angle of optical rotation $$\theta s = \{a \cdot x - b \cdot e1\}$$

gradually decreases in value, but when the light incident on the linearly polarized light detecting means 224 is elliptically polarized light, Vdt does not become equal to 0. In this condition, Vdt is amplified to create the voltage e1 for driving the optical rotation controlling liquid crystal element 204, and when e1 is increased to reduce Vdt down to 0, θs0 drops below the minimum point and, after that, the control enters a positive feedback region in which Vdt increases with increasing e1.

Accordingly, the compensating control operation is performed by preliminarily adjusting the output of the linearly polarized light detecting means 224 by controlling the optical rotation control element 204 and the phase compensating element 205 in sequence. In the negative feedback for the driving voltage e1 of the optical rotation controlling liquid crystal element 204 also, an e1 point at which Vdt is minimum is found by successively increasing and decreasing the driving voltage and, at that point, an extreme value e2 at which Vdt is minimum is found, this time by successively increasing and decreasing the driving voltage of the phase control element 205; next, e1 and e2, where Vdt is minimum, are fine-adjusted.

If there is no interference of external light, the angle of optical rotation is proportion to the sugar concentration in the sample and the light path length of the sample. The simplest way to maintain the light path length constant is to fix the physical dimensions of the sample in FIG. 1. Further, in order to keep control of the amount of blood in the fixed volume of the sample, if the amount of attenuation of light passing through the sample is measured, and the angle of optical rotation is divided by the amount of attenuation, the effects of the variation of the blood amount in the body part being measured can be reduced.

If there is interference from external light, it is most important and useful to remove light of other wavelengths than the wavelength of the laser diode light source that is used for the measurement of the blood sugar concentration. For this purpose, if the laser diode is a red light emitting type, it is effective to attach to the front of the polarized light intensity detecting element a means that blocks light of other wavelengths than the red light. When using an infrared laser light source, a filter is used that blocks or absorbs light of wavelengths shorter than the wavelength of that light source.

Figure 11:
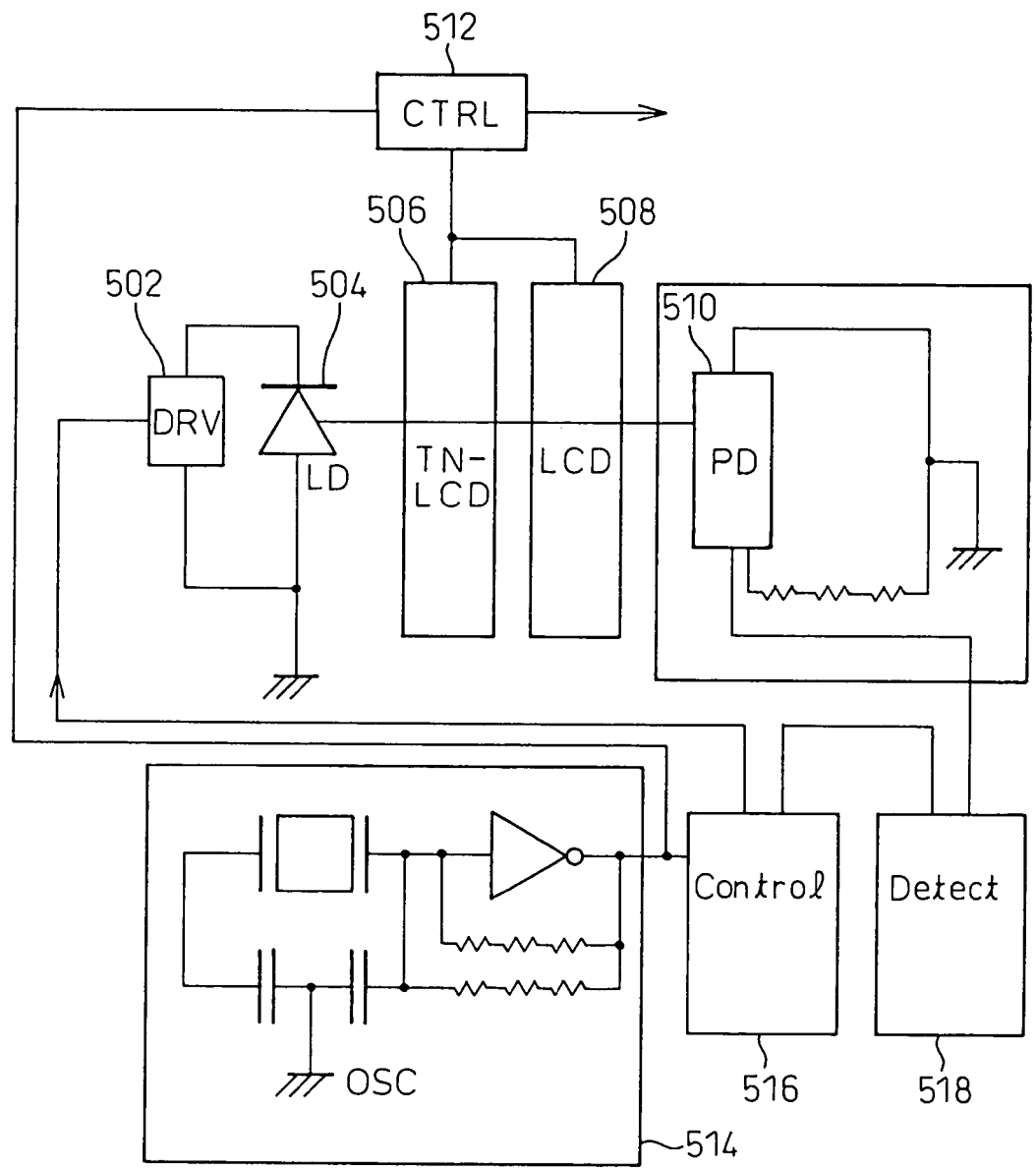
FIG. 11 is a block diagram showing the configuration of a concentration measuring apparatus according to an eighth embodiment of the present invention.

FIG. 11 shows the configuration of a control system for the measurement of optically active substance concentration according to one embodiment of the present invention. The entire system comprises: a linearly polarized light source 504 which includes a laser diode; an optical rotation controlling liquid crystal element 506; a phase modulating liquid crystal element 508; a light detecting means 510 constructed from a combination of a linear polarizer and a light detecting element; a drive control circuitry 516 for frequency- or code-modulating the laser diode in the linearly polarized light source 504; a drive circuitry 502 for driving the laser diode; a detection circuitry 518 for analyzing an output signal of the light detecting means 510, and for extracting optical rotation information; a liquid crystal drive circuitry 512 for driving the optical rotation controlling liquid crystal element 506 and the phase modulating liquid crystal element 508; and an oscillator circuitry 514 for providing a common time reference which is used in common for controlling the drive circuitries 502 and 512 and the detection circuitry 518.

Based on the clock signal of a constant and accurate frequency created by the oscillator circuitry 514 constructed from a crystal oscillator circuit, etc. the drive control circuitry 516 creates a control signal for modulating the output light of the linearly polarized light source 504, and drives the light source 504 via the light source driving circuit 502. In the detection circuitry 518 which extracts optical rotation information by using the synchronized time reference signal created by the same oscillator 514, the detection signal of the light detecting means 510 is analyzed, and the optically active sample concentration is computed.

The detection signal component can be extracted with a high S/N ratio by, for example, frequency-modulating the light source 504 in accordance with a predefined rule, by extracting in the detection circuitry 518 the detection signal through a narrowband extraction filter matched to the light source modulating frequency, and by detecting the signal in synchronism with a clock signal of the same frequency. The method of synchronous detection and the method of coded modulation/demodulation are effective in measuring the concentration of the optically active substance by eliminating the effects of the various electrical noise and optical noise that the person under examination encounters, and the generation and utilization of the common clock signal is also effective.

Figure 12:
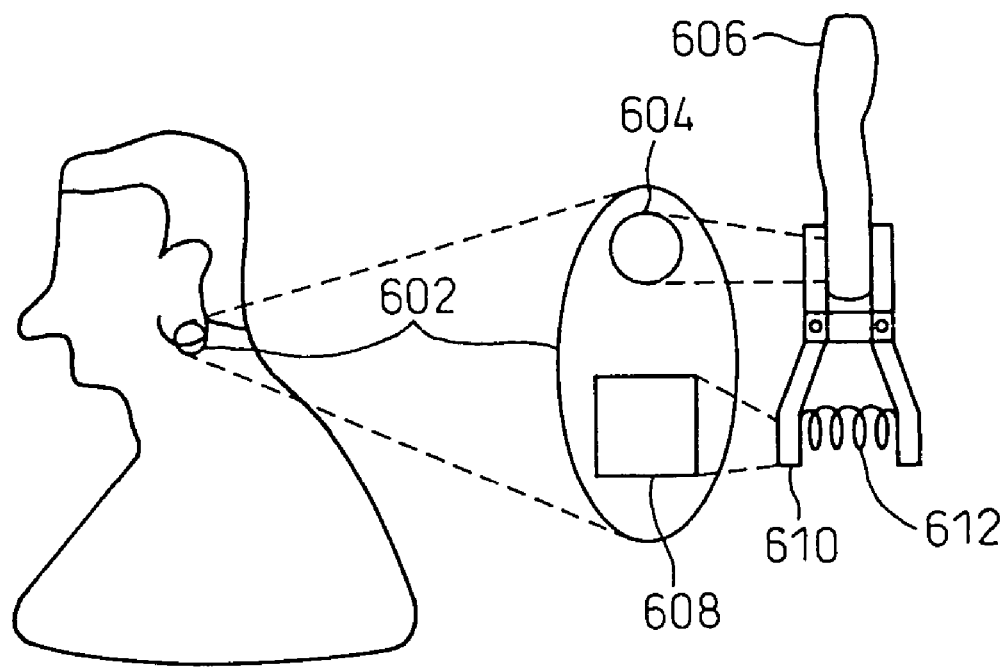
FIG. 12 is a schematic diagram showing the configuration of a concentration measuring apparatus according to a ninth embodiment of the present invention.

FIG. 12 shows an example in which the sugar concentration detection apparatus of the invention is worn on a human body. To keep the measuring light path length constant, it is effective to use a mechanical member that can clamp a body part at a constant thickness. For example, the sample is clamped using a spring mechanism such as a clothespin; in this case, a protrusion or a clamp member for limiting the clamp travel distance is provided on the spring side or the clamping side, to maintain the thickness of the clamped part substantially constant. In FIG. 12, reference numeral 602 is a concentration measuring apparatus which is clamped on the earlobe, and 604 is a module in which a polarized light emitting element and a polarized light detecting element are integrated; the opposite side of the clamping member is a mirrored surface. Polarized light emitted from the light emitting element is passed through the body part and reflected by the mirrored surface, and the reflected light is again passed through the body part and enters the polarized light detecting element. Reference numeral 608 is a circuit module which contains a signal processing circuit, a power supply cell, and a wireless transmitter, and is incorporated in the earlobe clamp-type concentration measuring apparatus. Reference numeral 606 is the earlobe. Reference numeral 610 is a clothespin-like member for clamping the earlobe, and 612 is a spring which generates the clamping force. The advantage of the earlobe clamp-type apparatus is that not only is the blood circulation through the earlobe relatively constant, but the apparatus does not cause any nuisance to the person who wears it on the earlobe. For a person who does not like to be seen wearing the apparatus, the apparatus may be worn on some other part of the body, such as the belly or a leg or an arm, that is covered by clothes.

To reduce power consumption, the measurement is made intermittently at predetermined intervals of time or at predetermined times under control of a clock, and the measured data are stored and are read out for use as necessary.

Figure 13:
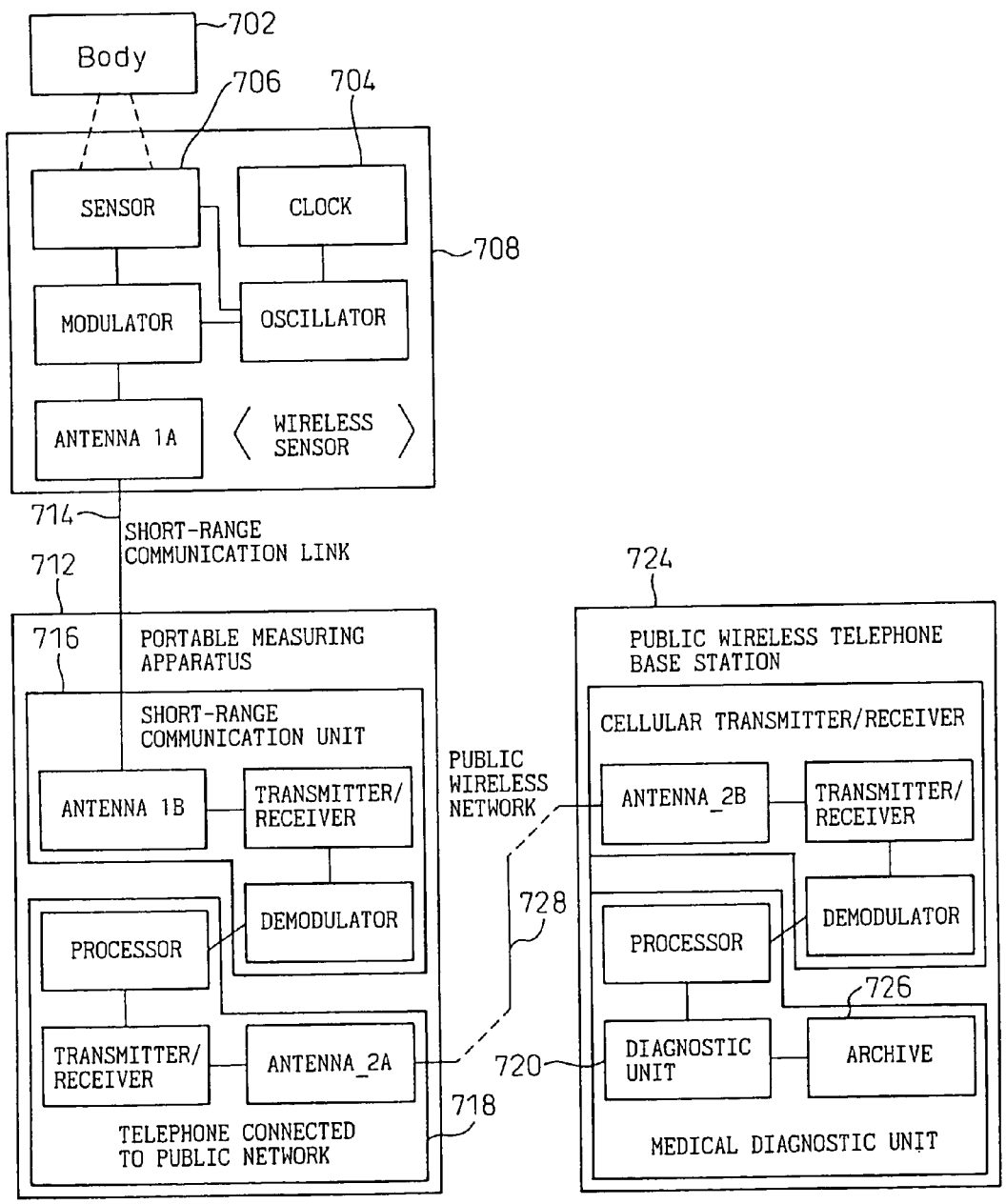
FIG. 13 is a block diagram showing the configuration of a concentration measuring apparatus according to a 10th embodiment of the present invention.

FIG. 13 shows an example of the system configuration when the sugar concentration detection apparatus of the invention is worn on a human body. In FIG. 13, considering the wearability, the sensor section is made up of the minimum necessary number of components including the power supply, and the collected detection information is transmitted to the main portable apparatus via a short-range wireless link. The main portable apparatus is constructed to be able to send the information via a public wireless telephone network to a patient biological information data bank so that the doctor can diagnose the information.

In FIG. 13, reference numeral 708 is a sensor module and, more specifically, is a wireless detection module, such as an earlobe clamp-type module like the one shown in FIG. 12 or a bracelet-type or bellyband-type module. Reference numeral 702 is a sample, 706 is the optically active substance concentration detecting element of the present invention, and 704 is a built-in clock which is synchronized to the clock incorporated in the main portable apparatus 712. Reference numeral 714 is a short-range communication link that uses weak radio waves or low-frequency magnetic waves lower than 10 kHz. Reference numeral 716 is a short-range receiver incorporated in the main portable sensing apparatus, and 718 is a main processing unit which includes a signal analyzer/processor and a wireless transmission/reception interfacing unit for interfacing with the public wireless telephone network. Reference numeral 728 is the public wireless telephone network, and 724 is a hospital system equipped with a patient tracking management/diagnosis function. The hospital system is also equipped with a hospital wireless base station function that uses the public wireless telephone network, so that the system can be linked to a large number of portable test apparatuses and can provide services when accessed by patients or monitor and manage contracted patients' conditions by tracking the patients. The communication base station function can be entrusted to a telephone company. Information is transmitted via the communication link 728 by establishing a bidirectional link between the portable apparatus and a cellular transmitter/receiver, and the patient's data is stored in an archive 726 provided in a medical diagnostic unit 720. As can be seen from the medical care system divided in the three sections as described above, biosensing is not limited to localized symptomatic therapy, but can be linked with an information analysis/comparison diagnostic system to provide additional benefits. It is also possible to achieve a mechanism that does not impose excessive functional or energy loads to the sensing module. The concentration detection system of the present invention that does not use any moving parts allows an extremely small and low-power construction, and is suited for application to a wearable wireless concentration detection apparatus or an implantable blood sugar concentration detection apparatus. The measurement is made intermittently, or by controlling the measurement period, to reduce average power consumption.

Figure 14:
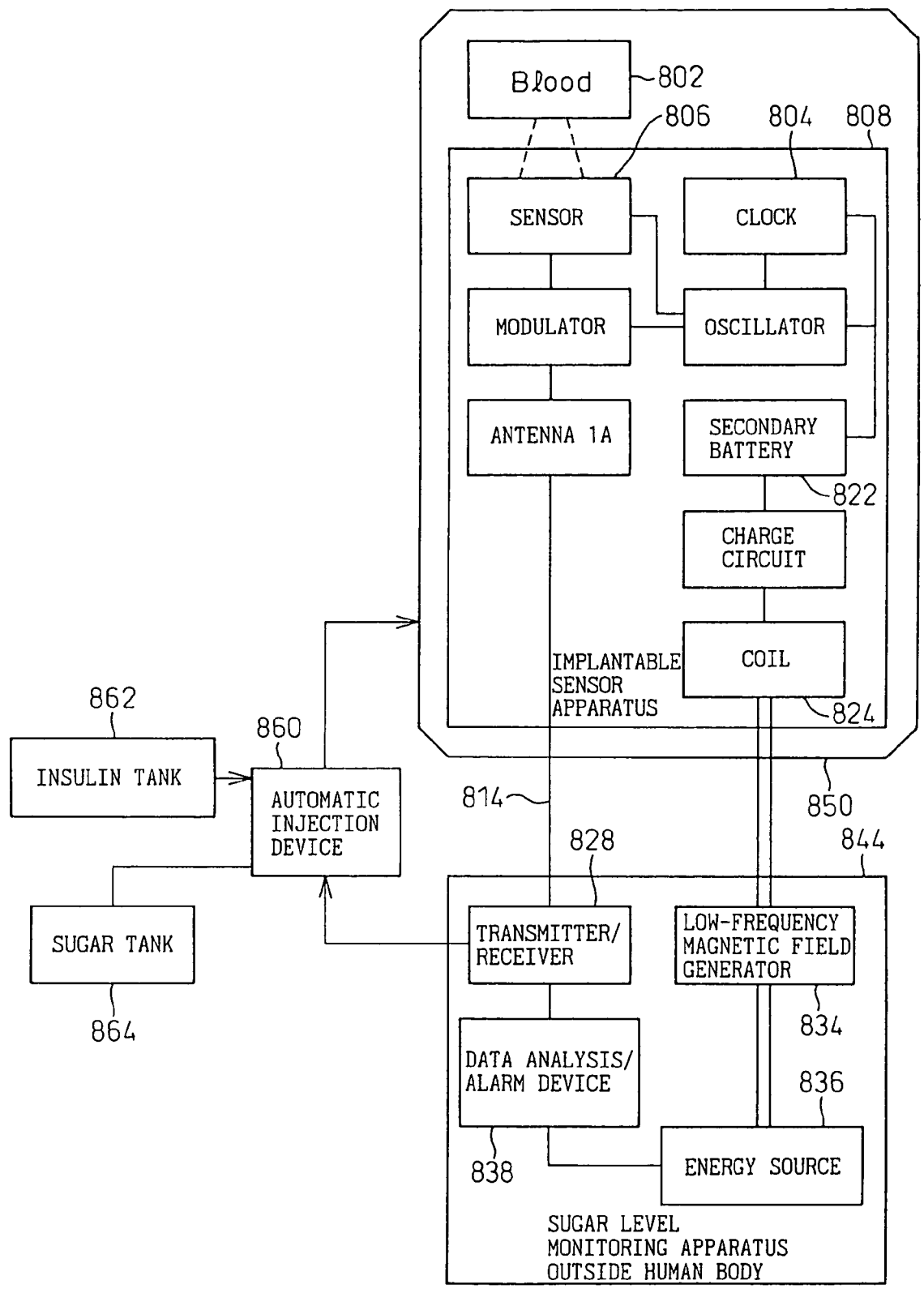
FIG. 14 is a block diagram showing the configuration of a concentration measuring apparatus according to an 11th embodiment of the present invention.

In FIG. 14 shows an example of the system configuration when the sugar concentration detection apparatus of the invention is implanted in a human body. In FIG. 14, one configuration example of the implantable blood sugar concentration detection apparatus is shown. Reference numeral 802 is a sample, 808 is the detection apparatus, 806 is a sensor element, 804 is a built-in clock, 822 is a secondary battery, and 824 is a charge coil. These, together with a transmitter 826 including an antenna, constitute an implantable sensor apparatus 850 to be implanted in the human body.

Reference numeral 844 is a sugar level monitoring apparatus external to the human body. The apparatus 844 is an information exchange apparatus that also serves as a battery charger, and is placed outside the human body. Reference numeral 834 is a low-frequency magnetic wave generator which generates magnetic waves lower in frequency than 10 kHz, and supplies electrical energy to the implanted sensor apparatus 850. Reference numeral 836 is an energy source for the battery charger, which derives power from a battery or a commercial power supply. Reference numeral 838 is a data analysis/alarm device which analyzes biological data input via a transmitter/receiver 828, and issues an alarm if the data indicates any abnormality in the human body; this device has a built-in clock which is synchronized to the clock built in the implanted sensor apparatus. The alarm condition may be indicated using, for example, a display device or by means of voice or vibration. The transmitter/receiver 828 transmits information to the implanted apparatus by using weak electromagnetic waves, and collects information from the apparatus. Reference numeral 814 is a short-range communication link.

The implanted sensor apparatus 850 constantly measures blood sugar concentration in vivo via a titanium metal case or a sapphire or silica light path that does not cause an allergic reaction on human body, and the implanted apparatus can transmit the results of the measurements in a safe manner to the apparatus outside the human body.

If an automatic injection device 860 and insulin and sugar spare reservoirs 862 and 864 are added in the above system, an injection of insulin or sugar can be automatically administered in an emergency situation. The automatic injection device and the insulin and sugar spare reservoirs are placed outside the human body and, depending on the biological information received from the implanted sensor apparatus 850, the data analysis/alarm device 838 in the sugar level monitoring apparatus 844 issues an alarm to the patient via the transmitter/receiver 828 or drives the automatic injection device 860 to automatically administer an injection of insulin or sugar. Alternatively, the sugar level monitoring apparatus 844 may be configured to monitor the implanted sensor apparatus 850 at predetermined intervals of time and to issue an alarm or drive the automatic injection device if any abnormality is detected.

Figure 15:
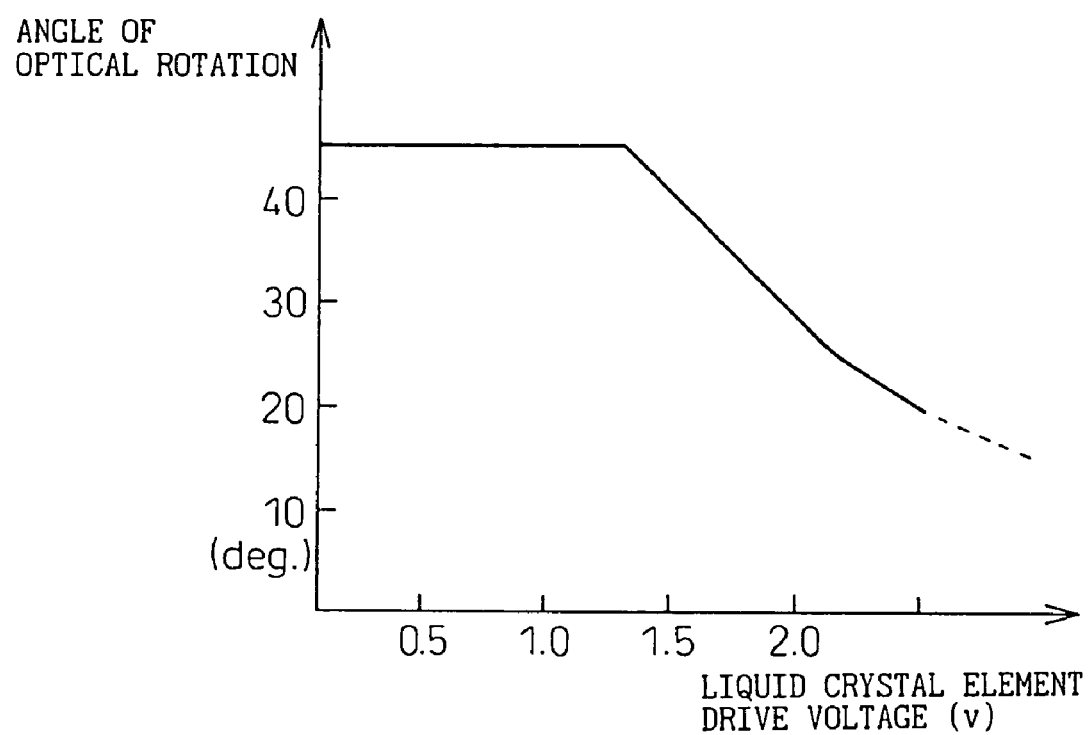
FIG. 15 is a diagram showing one example of the optical rotation control characteristic of the optical rotation controlling liquid crystal element used in the concentration measuring apparatus of the present invention.

FIG. 15 shows one example of the characteristic of the optical rotation control element used in the present invention. The graph here shows the characteristic when AC pulses of 32 kHz are applied to the liquid crystal element that exhibits a 45-degree twisted structure at an applied voltage of 0. When the applied voltage is not higher than 1.5 V, the liquid crystal produces an optical rotation of 45 degrees, but when the drive voltage exceeds 1.5 V, the angle of optical rotation monotonically decreases until the voltage reaches about 2 V.

Figure 16B:
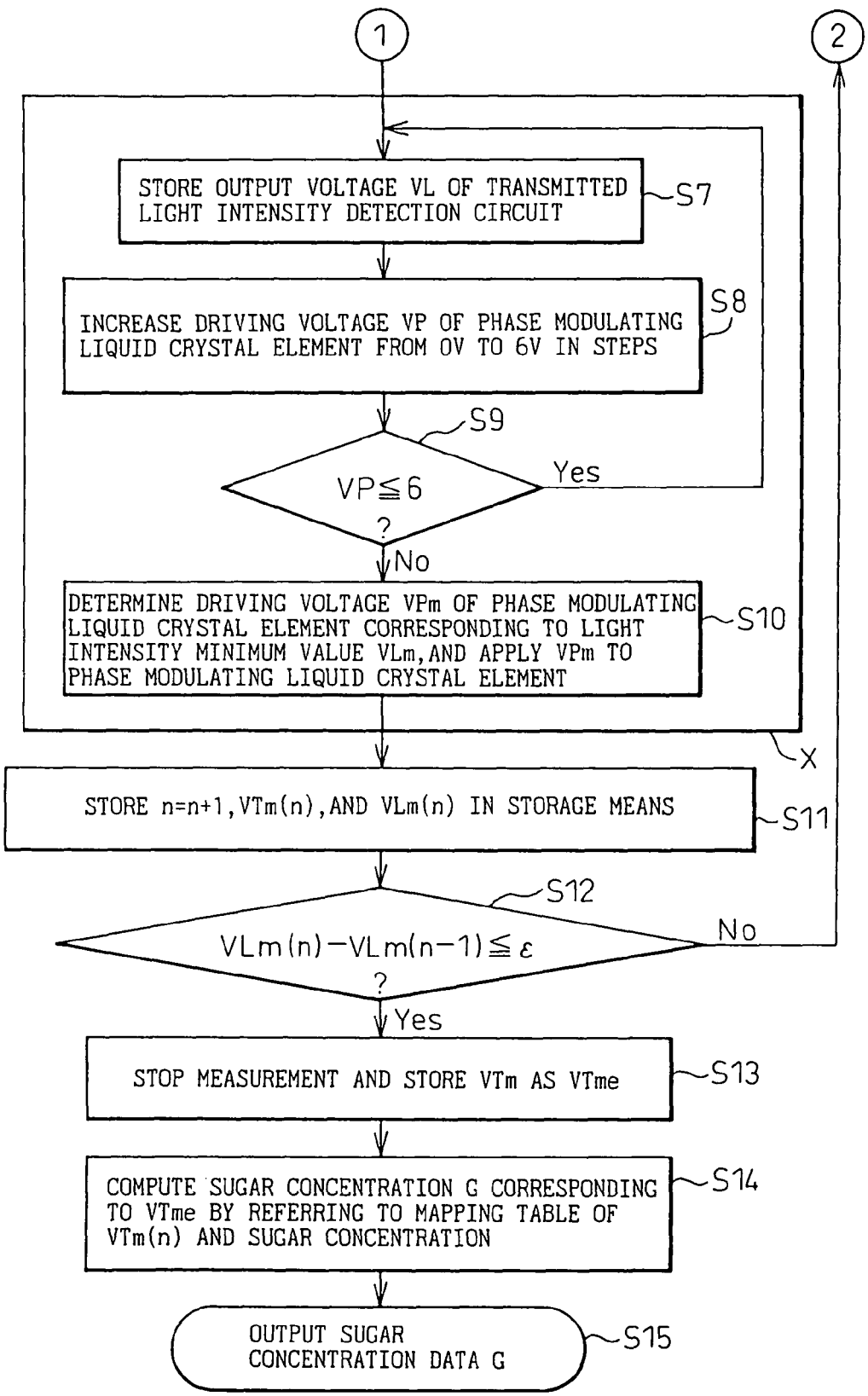
FIG. 16B is a diagram showing the second half of the flowchart illustrating the procedure for measuring sugar concentration in a solution by using the concentration measuring apparatus shown in FIG. 1.

FIG. 16 is a flowchart illustrating a procedure for measuring sugar concentration in a solution by using the concentration measuring apparatus shown in FIG. 1. FIG. 16A shows the first half of the flowchart, and FIG. 16B shows the second half. The concentration measuring procedure will be described below with reference to the flowchart.

The measuring system setup before the start of the measurement will be described first. In the measuring apparatus, the laser diode, i.e., the linearly polarized light source, is placed in position and, on the upstream side of the light source as viewed in the light emitting direction, a transparent container containing an analyte solution is placed with its plane perpendicular to the output light of the diode. The angle of the linear polarization plane of the laser light is tentatively assumed to be 0 degree. The container containing the dextrorotatory analyte solution is followed by a $-\alpha$-degree twisted nematic liquid crystal element having a left-hand twisted structure. The $-\alpha$-degree twisted nematic liquid crystal element is followed by a linear polarizer whose polarization plane is oriented at right angles to the polarization plane of the exit polarizer of the $-\alpha$-degree twisted nematic liquid crystal element, and a light detecting element is placed on the exit side of the linear polarizer.

If the container is empty, the detection light is blocked by the twisted nematic liquid crystal element when the applied voltage is 0; at this time, the light detection circuit is outputting a signal indicating a light intensity level of 0. (The value of this 0-level signal is stored as VL0 in a storage circuit.) In this condition, an analyte solution is introduced into the container.

When the analyte solution is introduced into the container, as optically active molecules are randomly oriented in the solution, molecules whose long axis direction coincides with the polarization direction of the linearly polarized light fully produce rotatory power, but molecules whose long axes are oriented at right angles to the polarization direction do not produce rotatory power, while molecules oriented in-between them produce intermediate rotatory power; on the average, a $+\beta$-degree optical rotation and elliptical polarization proportional to the concentration are produced. In the case of a sugar solution which is dextrorotatory, a left-hand twisted nematic liquid crystal is the logical choice for the liquid crystal element, for ease of use.

After setting up the measuring apparatus as described above, the concentration measurement is started in step S1 in FIG. 16. At this time, various memories in the measuring apparatus are initialized. At the same time, counter value n is set to 0.

In the next step S2, the light-emitting diode is turned on, and various initial values of the measuring system are checked and stored. Then, in step S3, the output value VL of the light measuring circuit is measured, and its initial value VL0 is stored.

Next, in steps S4 and S5, the AC drive voltage applied to the twisted nematic liquid crystal element (one that produces an optical rotation of several tens of degrees at an applied voltage of 0) is increased in steps from V1 (=0 V) to V2 (=2 V). That is, it is determined in step S5 whether the drive voltage VT has reached 2 V and, if the voltage has not reached 2 V yet (No), the process returns to step S3 to measure the light intensity at that instant in time. The measured value VL is stored with the applied voltage VT as its address value.

At the applied voltage of 0, because of the optical activity of the analyte solution the plane of polarization is rotated through $\beta$ degrees, and elliptical polarization also occurs, causing leakage of light. Here, when the applied voltage to the $-\alpha$ twisted nematic liquid crystal element is increased, the $-\alpha$ optical rotation component decreases, and as a result, the light emerging from the liquid crystal element is elliptically polarized light. As the applied voltage increases, the light component passing through the linear polarizer first decreases due to the above effect and, then, increases. The applied voltage to the twisted nematic liquid crystal element at which the transmitted light takes a minimum value increases with increasing sugar concentration.

By the time the applied voltage is swept from V1 to V2, the twisted nematic liquid crystal drive voltage VTm at which the measured value takes a minimum value has almost been determined. Due to measurement errors, it is not easy to accurately determine the twisted nematic liquid crystal drive voltage at which the transmitted light takes a minimum value. A relatively simply method is to make use of the fact that the step size with which the drive voltage is incrementally increased is predetermined, and to apply smoothing in which a moving average of the liquid crystal drive voltage at 21 neighboring points is taken and the measured light intensity value corresponding to that average value is determined as the corrected measured value of the 11th point located at the midpoint of the 21-point span; then, the drive voltage that minimizes the corrected measured value is defined as the twisted nematic liquid crystal drive voltage VTm that yields the light intensity minimum value VLm, and this voltage value VTm is applied to the twisted nematic liquid crystal element (step S6).

When the liquid crystal element is thus set to minimize the amount of transmitted light as described above, if a phase modulating liquid crystal element is placed between the twisted nematic liquid crystal element and the polarizer to adjust the phase difference, the minimum value of the transmitted light further decreases. This phase compensation is applied in order to enhance the accuracy when determining the minimum value of the light transmittance of the twisted nematic liquid crystal, but in the case of an apparatus that does not use the phase modulating liquid crystal element, for example, the apparatus of the first embodiment shown in FIG. 1, the following step X is omitted.

In the step X of obtaining the optimum phase modulation voltage VPm, the output voltage VL of the light detection circuit when the twisted nematic liquid crystal drive voltage is VTm is stored in step S7. Next, in steps S8 to S10, the voltage VP applied to the phase modulating liquid crystal element is increased in steps from 0 V to 6 V, and the voltage value VPm at which the output voltage VL takes a minimum value is detected and is applied to the phase modulating liquid crystal element.

In step S11, the number of measurements, n, is stored together with the voltage value VTm(n) and output voltage value VLm(n) obtained in the above steps.

Next, in step S12, the degree of convergence is checked. More specifically, in the (n−1)th and n-th measurements, VLm(n)−VLm(n−1) is obtained, and the measurement is repeated until the obtained value converge within a predetermined error $\epsilon$. That is, as long as the data of the twisted nematic liquid crystal drive voltage VTm that maintains the transmitted light at a minimum varies greatly between measurements as the number of measurements, n, increases, the process returns to step S3 to repeat the measurement, and when the result of the measurement has settled within the predetermined error $\epsilon$, the measurement is stopped (Yes in step S12).

Next, in step S13, the value of the applied voltage VTm at that instant in time is store as "VTme", and in step S14, the sugar solution concentration corresponding to the value VTme is computed from a mapping table of value VTme and sugar concentration. In step S15, the sugar concentration data G thus computed is output.

One example of the sugar concentration measuring procedure has been described above.

In the above measurement, noise signals superimposed on measured values, light intensity measurement errors, variations in the position of the sensor worn on the human subject, and light noise from outside the human body are the factors that limit the sugar concentration measurement. To eliminate the effects of these limiting factors, smoothing operations based on time averages and averaging operations appropriate to the conditions near the measured values are performed. In the moving average method, while the liquid crystal drive voltage is being swept from 0 V to 20 V in 200 steps each with a step size of 10 mV, the average of neighboring 11 data points is taken and the sixth data point located at the midpoint of the 11-point span is replaced by the average value of the neighboring 11 data points; when this moving average method is used, data from the sixth data point to the 194th data points are replaced by the data smoothed by the above moving average process. Each moving average data has about one-tenth of the error occurring at the time of the measurement. As the point here is not to obtain the minimum value itself but to accurately determine the value of the applied voltage that yields the minimum value, the above smoothing is effective in eliminating the effects of sporadic noise. Further, if neighboring data near the extreme value of the smoothed 188 data values are selected, and a simple function such as a quadratic function is applied using the method of least squares, then by differentiating this function the value of the applied voltage at which the extreme value occurs can be accurately estimated. By so doing, the minimum value can be computed in a simple manner, based on the smoothed data.

The above measuring procedure can be applied to a system in which a laser light emitting element and a laser light reflecting member are mounted on a toilet stool and the reflected light is detected by a twisted nematic liquid crystal element and a light detecting element to measure the angle of optical rotation. Since the flush toilet is flushed every time it is used, and since there always remains a certain amount of water in the toilet bowl, the degree of dilution of urine can be estimated by measuring the water level, and the sugar concentration can thus be corrected.

The above description can be summarized as follows. That is, a liquid crystal element exhibiting a twisted structure can be used as an electronically controllable optically active element, since it has an ability to rotate the component of light that lies along the principal axis of the molecular orientation. When a voltage is applied, the light is elliptically polarized; therefore, the elliptically polarized light can be converted into linearly polarized light by using a parallel aligned liquid crystal element that controls the phase difference between the two birefringent components.

With the parallel aligned liquid crystal element whose orientation direction is twisted several tens of degrees, for example, 45 degrees, with respect to the major axis of the elliptically polarized light, the elliptically polarized light can be converted into linearly polarized light by electrically adjusting the phase difference between the major axis and minor axis components of the elliptically polarized light by utilizing the velocity difference between the major axis component and the minor axis component propagating at different velocities through the parallel aligned liquid crystal element.

By combining the above two optical control elements, the concentration of an optically active substance dissolved in a solution can be measured in a relative manner. Even in the case of the measurement of optical rotation buried in noise, such as the measurement of blood sugar concentration in a human body, information concerning the plane of polarization can be extracted as it is different from light intensity information.

When using the apparatus of the invention as a health management support tool for an individual, if the individual can check the condition of his health against his normal healthy condition, it will suffice the purpose of health management even if the measurement contains a certain degree of error. Blood sugar detection by electronic control of the optically active liquid crystal element allows a compact and low-power construction, and is suited for a wearable or implantable apparatus.

To extract the measuring signal buried in noise, it is effective to use a wavelength filter that transmits only the wavelength of the measuring laser light source and blocks or absorbs other wavelengths that degrade the sensitivity of the measurement. Furthermore, by also using software processing based on a coded time averaging method and thereby improving the signal-to-noise ratio of the measurement, polarization component information buried in noise, from the blood under the skin, can be extracted.

In applications that do not require enhanced accuracy but can do with a simple measurement, sugar concentration in urine, etc. can be measured in a simple way by using the method of the present invention. If the measuring apparatus of the invention is adapted to be implantable in a human body, blood sugar concentration can be measured accurately, which is very useful.

ADVANTAGEOUS EFFECT OF THE INVENTION

As the concentration of an optically active substance in a solution can be measured by electronically controlling the liquid crystal optical element, the invention achieves a sugar concentration measuring apparatus having excellent portability and compact in construction. The low-power design allows the construction of a wearable or implantable apparatus. As there is no moving part, the apparatus does not generate dust and is capable of stable operation over an extended period of time.

What is claimed is:

1. A concentration measuring apparatus comprising:
   a light source for outputting linearly polarized light;
   a light intensity detecting element disposed opposite said light source across a sample placed therebetween;
   an optically active liquid crystal element placed between said light source and said light intensity detection element;
   a control circuit which controls a voltage to be applied to said optically active liquid crystal element so that an output value from said light intensity detecting element will, in effect, take an extreme value;
   a concentration computing circuit for computing the concentration of an optically active substance in said sample, based on an output from said control circuit; and
   a phrase modulating element placed between said light source and said light intensity detecting element, wherein the phase modulating element is formed from a liquid crystal.

2. A concentration measuring apparatus as claimed in claim 1, wherein said control circuit includes:
   a code modulation circuit for controlling said light source in such a manner that light to be output from said light source is modulated with a particular code, and
   a filter circuit for extracting said modulated light component from an output of said light intensity detecting element.

3. A concentration measuring apparatus as claimed in claim 1, wherein said control circuit includes:

a code modulation circuit for controlling said light source in such a manner that light to be output from said light source is modulated with a particular frequency, and a filter circuit for extracting said modulated light component from an output of said light intensity detecting element.

4. A concentration measuring apparatus as claimed in claim 1, further comprising:

a first wavelength selective filter for selecting output light of said light source with a particular frequency; and a second wavelength selective filter for allowing only the light passed through said first wavelength selective filter to reach said light intensity detecting element.

5. A concentration measuring apparatus as claimed in claim 1, wherein said light source is a solid-state laser element that emits linearly polarized light.

6. A concentration measuring apparatus as claimed in claim 1, wherein said sample is blood and said optically active substance is sugar.

7. A concentration measuring apparatus as claimed in claim 1, further comprising a monitor circuit for monitoring an output of said concentration computing circuit at predetermined intervals of time, and for generating an alarm signal when said monitored concentration value exceeds a predetermined value.

8. A concentration measuring apparatus as claimed in claim 1, further comprising:

a transmitter for transmitting an output of said control circuit; and a receiver for receiving a signal transmitted from said transmitter, and for supplying said received signal to said computing circuit, and wherein:

said light source, said light intensity detecting element, said optically active liquid crystal element, said control circuit, and said transmitter are implanted in a human body.

9. A concentration measuring apparatus as claimed in claim 7, further comprising automatic insulin injecting means which is driven by said alarm signal.

10. A concentration measuring apparatus as claimed in claim 7, further comprising automatic sugar injecting means which is driven by said alarm signal.

* * * * *